United States Patent
Call et al.

(10) Patent No.: US 9,668,714 B2
(45) Date of Patent: Jun. 6, 2017

(54) SYSTEMS AND METHODS FOR IMPROVING ULTRASOUND IMAGE QUALITY BY APPLYING WEIGHTING FACTORS

(71) Applicant: Maui Imaging, Inc., Sunnyvale, CA (US)

(72) Inventors: Josef R. Call, Campbell, CA (US); Donald F. Specht, Los Altos, CA (US); Kenneth D. Brewer, Santa Clara, CA (US)

(73) Assignee: MAUI IMAGING, INC., Sunnyvale, CA (US)

( * ) Notice: Subject to any disclaimer, the term of this patent is extended or adjusted under 35 U.S.C. 154(b) by 420 days.

(21) Appl. No.: 13/850,823

(22) Filed: Mar. 26, 2013

(65) Prior Publication Data

US 2013/0253325 A1  Sep. 26, 2013

Related U.S. Application Data

(60) Provisional application No. 61/615,735, filed on Mar. 26, 2012.

(51) Int. Cl.
*A61B 8/14* (2006.01)
*G01S 15/89* (2006.01)
(Continued)

(52) U.S. Cl.
CPC ............ *A61B 8/145* (2013.01); *A61B 8/4477* (2013.01); *A61B 8/5253* (2013.01);
(Continued)

(58) Field of Classification Search
None
See application file for complete search history.

(56) References Cited

U.S. PATENT DOCUMENTS

| 3,174,286 A | 3/1965 | Erickson |
| 3,895,381 A | 7/1975 | Kock |

(Continued)

FOREIGN PATENT DOCUMENTS

| CN | 1781460 | 6/2006 |
| CN | 101116622 A | 2/2008 |

(Continued)

OTHER PUBLICATIONS

Smith et al.; U.S. Appl. No. 14/210,015 entitled "Alignment of ultrasound transducer arrays and multiple aperture probe assembly," filed Mar. 13, 2014.

(Continued)

*Primary Examiner* — Katherine Fernandez
*Assistant Examiner* — Kevin Pontius
(74) *Attorney, Agent, or Firm* — Shay Glenn LLP

(57) ABSTRACT

Systems and methods for improving the quality of ultrasound images made up of a combination of multiple sub-images include giving more weight to sub-image information that is more likely to improve a combined image quality. Weighting factor information may be determined from the geometry (e.g., angle or path length) of a location of one or more specific transducer elements relative to a specific point within a region of interest or a region of an image. In some embodiments, any given pixel (or other discrete region of an image) may be formed by combining received echo data in a manner that gives more weight to data that is likely to improve image quality, and/or discounting or ignoring data that is likely to detract from image quality (e.g., by introducing noise or by increasing point spread).

12 Claims, 9 Drawing Sheets

(51) Int. Cl.
*G01S 7/52* (2006.01)
*A61B 8/00* (2006.01)
*A61B 8/08* (2006.01)

(52) U.S. Cl.
CPC ...... *G01S 7/52046* (2013.01); *G01S 15/8927* (2013.01); *G01S 15/8952* (2013.01); *A61B 8/4245* (2013.01); *A61B 8/4427* (2013.01); *A61B 8/4488* (2013.01); *A61B 8/5207* (2013.01); *A61B 8/54* (2013.01); *G01S 7/52063* (2013.01); *G01S 15/8913* (2013.01)

(56) References Cited

U.S. PATENT DOCUMENTS

| | | | |
|---|---|---|---|
| 3,974,692 | A | 8/1976 | Hassler |
| 4,055,988 | A | 11/1977 | Dutton |
| 4,072,922 | A | 2/1978 | Taner et al. |
| 4,097,835 | A | 6/1978 | Green |
| 4,105,018 | A | 8/1978 | Greenleaf et al. |
| 4,180,792 | A | 12/1979 | Lederman et al. |
| 4,259,733 | A | 3/1981 | Taner et al. |
| 4,265,126 | A | 5/1981 | Papadofrangakis et al. |
| 4,271,842 | A | 6/1981 | Specht et al. |
| 4,325,257 | A | 4/1982 | Kino et al. |
| 4,327,738 | A | 5/1982 | Green et al. |
| 4,333,474 | A | 6/1982 | Nigam |
| 4,339,952 | A | 7/1982 | Foster |
| 4,452,084 | A | 6/1984 | Taenzer |
| 4,501,279 | A | 2/1985 | Seo |
| 4,511,998 | A | 4/1985 | Kanda et al. |
| 4,539,847 | A | 9/1985 | Paap |
| 4,566,459 | A | 1/1986 | Umemura et al. |
| 4,567,768 | A | 2/1986 | Satoh et al. |
| 4,604,697 | A | 8/1986 | Luthra et al. |
| 4,662,222 | A | 5/1987 | Johnson |
| 4,669,482 | A | 6/1987 | Ophir |
| 4,682,497 | A | 7/1987 | Sasaki |
| 4,781,199 | A | 11/1988 | Hirama et al. |
| 4,817,434 | A | 4/1989 | Anderson |
| 4,831,601 | A | 5/1989 | Breimesser et al. |
| 4,893,284 | A | 1/1990 | Magrane |
| 4,893,628 | A | 1/1990 | Angelsen |
| 5,050,588 | A | 9/1991 | Grey et al. |
| 5,141,738 | A | 8/1992 | Rasor et al. |
| 5,161,536 | A | 11/1992 | Vilkomerson et al. |
| 5,197,475 | A | 3/1993 | Antich et al. |
| 5,226,019 | A | 7/1993 | Bahorich |
| 5,230,339 | A | 7/1993 | Charlebois |
| 5,269,309 | A | 12/1993 | Fort et al. |
| 5,278,757 | A | 1/1994 | Hoctor et al. |
| 5,293,871 | A | 3/1994 | Reinstein et al. |
| 5,299,576 | A | 4/1994 | Shiba |
| 5,301,674 | A | 4/1994 | Erikson et al. |
| 5,305,756 | A | 4/1994 | Entrekin et al. |
| 5,339,282 | A | 8/1994 | Kuhn et al. |
| 5,340,510 | A | 8/1994 | Bowen |
| 5,345,426 | A | 9/1994 | Lipschutz |
| 5,349,960 | A | 9/1994 | Gondo |
| 5,355,888 | A | 10/1994 | Kendall |
| 5,398,216 | A | 3/1995 | Hall et al. |
| 5,409,010 | A | 4/1995 | Beach et al. |
| 5,442,462 | A | 8/1995 | Guissin |
| 5,454,372 | A | 10/1995 | Banjanin et al. |
| 5,503,152 | A | 4/1996 | Oakley et al. |
| 5,515,853 | A | 5/1996 | Smith et al. |
| 5,515,856 | A | 5/1996 | Olstad et al. |
| 5,522,393 | A | 6/1996 | Phillips et al. |
| 5,526,815 | A | 6/1996 | Granz et al. |
| 5,544,659 | A | 8/1996 | Banjanin |
| 5,558,092 | A | 9/1996 | Unger et al. |
| 5,564,423 | A | 10/1996 | Mele et al. |
| 5,568,812 | A | 10/1996 | Murashita et al. |
| 5,570,691 | A | 11/1996 | Wright et al. |
| 5,581,517 | A | 12/1996 | Gee et al. |
| 5,625,149 | A | 4/1997 | Gururaja et al. |
| 5,628,320 | A | 5/1997 | Teo |
| 5,673,697 | A | 10/1997 | Bryan et al. |
| 5,675,550 | A | 10/1997 | Ekhaus |
| 5,720,291 | A | 2/1998 | Schwartz |
| 5,720,708 | A | 2/1998 | Lu et al. |
| 5,744,898 | A | 4/1998 | Smith et al. |
| 5,769,079 | A | 6/1998 | Hossack |
| 5,784,334 | A | 7/1998 | Sena et al. |
| 5,785,654 | A | 7/1998 | Iinuma et al. |
| 5,795,297 | A | 8/1998 | Daigle |
| 5,797,845 | A | 8/1998 | Barabash et al. |
| 5,798,459 | A | 8/1998 | Ohba et al. |
| 5,820,561 | A | 10/1998 | Olstad et al. |
| 5,838,564 | A | 11/1998 | Bahorich et al. |
| 5,850,622 | A | 12/1998 | Vassiliou et al. |
| 5,862,100 | A | 1/1999 | VerWest |
| 5,870,691 | A | 2/1999 | Partyka et al. |
| 5,876,342 | A | 3/1999 | Chen et al. |
| 5,891,038 | A | 4/1999 | Seyed-Bolorforosh et al. |
| 5,892,732 | A | 4/1999 | Gersztenkorn |
| 5,916,169 | A | 6/1999 | Hanafy et al. |
| 5,919,139 | A | 7/1999 | Lin |
| 5,920,285 | A | 7/1999 | Benjamin |
| 5,930,730 | A | 7/1999 | Marfurt et al. |
| 5,940,778 | A | 8/1999 | Marfurt et al. |
| 5,951,479 | A | 9/1999 | Holm et al. |
| 5,964,707 | A | 10/1999 | Fenster et al. |
| 5,969,661 | A | 10/1999 | Benjamin |
| 5,999,836 | A | 12/1999 | Nelson et al. |
| 6,007,499 | A | 12/1999 | Martin et al. |
| 6,013,032 | A | 1/2000 | Savord |
| 6,014,473 | A | 1/2000 | Hossack et al. |
| 6,048,315 | A | 4/2000 | Chiao et al. |
| 6,049,509 | A | 4/2000 | Sonneland et al. |
| 6,050,943 | A | 4/2000 | Slayton et al. |
| 6,056,693 | A | 5/2000 | Haider |
| 6,058,074 | A | 5/2000 | Swan et al. |
| 6,077,224 | A | 6/2000 | Lang et al. |
| 6,092,026 | A | 7/2000 | Bahorich et al. |
| 6,122,538 | A | 9/2000 | Sliwa, Jr. et al. |
| 6,123,670 | A | 9/2000 | Mo |
| 6,129,672 | A | 10/2000 | Seward et al. |
| 6,135,960 | A | 10/2000 | Holmberg |
| 6,138,075 | A | 10/2000 | Yost |
| 6,148,095 | A | 11/2000 | Prause et al. |
| 6,162,175 | A | 12/2000 | Marian, Jr. et al. |
| 6,166,384 | A | 12/2000 | Dentinger et al. |
| 6,166,853 | A | 12/2000 | Sapia et al. |
| 6,193,665 | B1 | 2/2001 | Hall et al. |
| 6,196,739 | B1 | 3/2001 | Silverbrook |
| 6,200,266 | B1 | 3/2001 | Shokrollahi et al. |
| 6,210,335 | B1 | 4/2001 | Miller |
| 6,213,958 | B1 | 4/2001 | Winder |
| 6,221,019 | B1 | 4/2001 | Kantorovich |
| 6,231,511 | B1 | 5/2001 | Bae |
| 6,238,342 | B1 | 5/2001 | Feleppa et al. |
| 6,246,901 | B1 | 6/2001 | Benaron |
| 6,251,073 | B1 | 6/2001 | Imran et al. |
| 6,264,609 | B1 | 7/2001 | Herrington et al. |
| 6,266,551 | B1 | 7/2001 | Osadchy et al. |
| 6,278,949 | B1 | 8/2001 | Alam |
| 6,289,230 | B1 | 9/2001 | Chaiken et al. |
| 6,299,580 | B1 | 10/2001 | Asafusa |
| 6,304,684 | B1 | 10/2001 | Niczyporuk et al. |
| 6,309,356 | B1 | 10/2001 | Ustuner et al. |
| 6,324,453 | B1 | 11/2001 | Breed et al. |
| 6,345,539 | B1 | 2/2002 | Rawes et al. |
| 6,361,500 | B1 | 3/2002 | Masters |
| 6,363,033 | B1 | 3/2002 | Cole et al. |
| 6,370,480 | B1 | 4/2002 | Gupta et al. |
| 6,374,185 | B1 | 4/2002 | Taner et al. |
| 6,394,955 | B1 | 5/2002 | Perlitz |
| 6,423,002 | B1 | 7/2002 | Hossack |
| 6,436,046 | B1 | 8/2002 | Napolitano et al. |
| 6,449,821 | B1 | 9/2002 | Sudol et al. |
| 6,450,965 | B2 | 9/2002 | Williams et al. |
| 6,468,216 | B1 | 10/2002 | Powers et al. |
| 6,471,650 | B2 | 10/2002 | Powers et al. |
| 6,475,150 | B2 | 11/2002 | Haddad |

(56) References Cited

U.S. PATENT DOCUMENTS

| | | |
|---|---|---|
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,277,383 B2 | 10/2012 | Specht |
| 8,279,705 B2 | 10/2012 | Choi et al. |
| 8,412,307 B2 | 4/2013 | Willis et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,506,487 B2 * | 8/2013 | Masuzawa .................. 600/443 |
| 8,532,951 B2 | 9/2013 | Roy et al. |
| 8,582,848 B2 | 11/2013 | Funka-Lea et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |

(56) References Cited

U.S. PATENT DOCUMENTS

| | | |
|---|---|---|
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262291 A1 | 11/2006 | Hess et al. |
| 2006/0262961 A1 | 11/2006 | Holsing et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178400 A1 | 7/2011 | Specht et al. |
| 2011/0201933 A1 | 8/2011 | Specht et al. |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0057428 A1 | 3/2012 | Specht et al. |
| 2012/0085173 A1 | 4/2012 | Papadopoulos et al. |
| 2012/0095343 A1 | 4/2012 | Smith et al. |
| 2012/0095347 A1 | 4/2012 | Adam et al. |
| 2012/0101378 A1 | 4/2012 | Lee |
| 2012/0114210 A1 | 5/2012 | Kim et al. |
| 2012/0116226 A1 | 5/2012 | Specht |
| 2012/0121150 A1 | 5/2012 | Murashita |
| 2012/0137778 A1 | 6/2012 | Kitazawa et al. |
| 2012/0141002 A1 | 6/2012 | Urbano et al. |
| 2012/0165670 A1 | 6/2012 | Shi et al. |
| 2012/0179044 A1 | 7/2012 | Chiang et al. |

(56) References Cited

U.S. PATENT DOCUMENTS

| | | |
|---|---|---|
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0035595 A1 | 2/2013 | Specht |
| 2013/0070062 A1 | 3/2013 | Fouras et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0172743 A1 | 7/2013 | Brewer et al. |
| 2013/0204136 A1 | 8/2013 | Duric et al. |
| 2013/0204137 A1 | 8/2013 | Roy et al. |
| 2013/0247350 A1 | 9/2013 | Specht et al. |
| 2013/0258805 A1 | 10/2013 | Hansen et al. |
| 2013/0261463 A1 | 10/2013 | Chiang et al. |
| 2014/0086014 A1* | 3/2014 | Kobayashi .......... G01S 7/52066 367/90 |
| 2014/0243673 A1 | 8/2014 | Anand et al. |
| 2015/0297184 A1 | 10/2015 | Specht |
| 2015/0374345 A1 | 12/2015 | Specht et al. |
| 2016/0095579 A1 | 4/2016 | Smith et al. |
| 2016/0135783 A1 | 5/2016 | Brewer et al. |
| 2016/0157833 A1 | 6/2016 | Smith et al. |
| 2016/0256134 A1 | 9/2016 | Specht et al. |

FOREIGN PATENT DOCUMENTS

| | | |
|---|---|---|
| CN | 101190134 A | 6/2008 |
| CN | 101453955 A | 6/2009 |
| CN | 101843501 A | 9/2010 |
| CN | 102018533 A | 4/2011 |
| CN | 102123668 | 7/2011 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 1462819 B1 | 7/2011 |
| EP | 2356941 A1 | 8/2011 |
| EP | 1979739 | 10/2011 |
| EP | 2385391 A2 | 11/2011 |
| EP | 2294400 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | S49-11189 A | 1/1974 |
| JP | S54-44375 A | 4/1979 |
| JP | S55-103839 A | 8/1980 |
| JP | 57-31848 A | 2/1982 |
| JP | 58-223059 A | 12/1983 |
| JP | 59-1011434 A | 6/1984 |
| JP | S59-174151 A | 10/1984 |
| JP | S60-13109 U | 1/1985 |
| JP | S60-68836 A | 4/1985 |
| JP | 2-501431 A | 5/1990 |
| JP | 03126443 A | 5/1991 |
| JP | 04017842 A | 1/1992 |
| JP | 4-67856 | 3/1992 |
| JP | 05-042138 A | 2/1993 |
| JP | 6-125908 A | 5/1994 |
| JP | 7-051266 A | 2/1995 |
| JP | 07204201 A | 8/1995 |
| JP | 08-252253 | 10/1996 |
| JP | 9-103429 A | 4/1997 |
| JP | 9-201361 A | 8/1997 |
| JP | 2777197 B | 5/1998 |
| JP | 10-216128 A | 8/1998 |
| JP | 11-089833 A | 4/1999 |
| JP | 11-239578 A | 9/1999 |
| JP | 2001-507794 A | 6/2001 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2005152187 A | 6/2005 |
| JP | 2005-523792 | 8/2005 |
| JP | 2005-526539 | 9/2005 |
| JP | 2006051356 A | 2/2006 |
| JP | 2006-61203 A | 3/2006 |
| JP | 2006-122657 A | 5/2006 |
| JP | 2006130313 A | 5/2006 |
| JP | 2007-325937 A | 12/2007 |
| JP | 2008-122209 | 5/2008 |
| JP | 2008-513763 A | 5/2008 |
| JP | 2008132342 A | 6/2008 |
| JP | 2008522642 A | 7/2008 |
| JP | 2008-259541 A | 10/2008 |
| JP | 2008279274 A | 11/2008 |
| JP | 20105375 | 1/2010 |
| JP | 2010124842 A | 6/2010 |
| JP | 2010526626 A | 8/2010 |
| KR | 100715132 B | 4/2007 |
| KR | 1020090103408 A | 10/2009 |
| WO | WO 92/18054 A1 | 10/1992 |
| WO | WO 98/00719 A2 | 1/1998 |
| WO | WO01/64109 A1 | 9/2001 |
| WO | WO02/084594 A2 | 10/2002 |
| WO | WO2005/009245 A1 | 2/2005 |
| WO | WO 2006/114735 A1 | 11/2006 |
| WO | WO 2007/127147 A2 | 11/2007 |
| WO | WO2009/060182 A2 | 5/2009 |
| WO | WO 2010/017445 A2 | 2/2010 |
| WO | WO 2010/095094 A1 | 8/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |
| WO | WO2013/116851 A1 | 8/2013 |
| WO | WO2013/116854 A1 | 8/2013 |
| WO | WO2013/116866 A1 | 8/2013 |
| WO | WO2013/128301 A2 | 9/2013 |

OTHER PUBLICATIONS

Hendee et al.; Medical Imaging Physics; Wiley-Liss, Inc. 4th Edition; Chap. 19-22; pp. 303-353; © 2002 (year of pub. sufficiently earlier than effective US filing date and any foreign priority date).
Wikipedia; Point cloud; 2 pages; Nov. 24, 2014; retrieved from the internet (https://en.wikipedia.org/w/index.php?title=Point_cloud&oldid=472583138).

(56) References Cited

OTHER PUBLICATIONS

Smith et al.; U.S. Appl. No. 14/526,186 entitled "Universal multiple aperture medical ultrasound probe," filed Oct. 28, 2014.
Smith et al.; U.S. Appl. No. 14/595,083 entitled "Concave ultrasound transducers and 3D arrays," filed Jan. 12, 2015.
Belevich et al.; U.S. Appl. No. 13/964,701 entitled "Calibration of Multiple Aperture Ultrasound Probes," filed Aug. 12, 2013.
Call et al.; U.S. Appl. No. 13/971,689 entitled "Ultrasound Imaging System Memory Architecture," filed Aug. 20, 2013.
Specht et al.; U.S. Appl. No. 14/279,052 entitled "Ultrasound imaging using apparent point-source transmit transducer," filed May 15, 2014.
Specht et al.; U.S. Appl. No. 14/078,311 entitled "Imaging with Multiple Aperture Medical Ultrasound and Synchronization of Add-On Systems," filed Nov. 12, 2013.
Specht, D. F.; U.S. Appl. No. 14/157,257 entitled "Method and Apparatus to Produce Ultrasonic Images Using Multiple Apertures," filed Jan. 16, 2014.
Cristianini et al.; An Introduction to Support Vector Machines; Cambridge University Press; pp. 93-111; Mar. 2000.
Du et al.; User parameter free approaches to multistatic adaptive ultrasound imaging; 5th IEEE International Symposium; pp. 1287-1290, May 2008.
Feigenbaum, Harvey, M.D.; Echocardiography; Lippincott Williams & Wilkins; Philadelphia; 5th Ed.; pp. 428, 484; Feb. 1994.
Haykin, Simon; Neural Networks: A Comprehensive Foundation (2nd Ed.); Prentice Hall; pp. 156-187; Jul. 16, 1998.
Kramb et al,.; Considerations for using phased array ultrasonics in a fully automated inspection system. Review of Quantitative Nondestructive Evaluation, vol. 23, ed. D. O. Thompson and D. E. Chimenti, pp. 817-825, (year of publication is sufficiently earlier than the effective U.S. filing date and any foreign priority date) 2004.
Ledesma-Carbayo et al.; Spatio-temporal nonrigid registration for ultrasound cardiac motion estimation; IEEE Trans. on Medical Imaging; vol. 24; No. 9; Sep. 2005.
Leotta et al.; Quantitative three-dimensional echocardiography by rapid imaging . . . ; J American Society of Echocardiography; vol. 10; No. 8; pp. 830-839; Oct. 1997.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Press et al.; Cubic spline interpolation; §3.3 in "Numerical Recipes in Fortran: The Art of Scientific Computing", 2nd Ed.; Cambridge, England; Cambridge University Press; pp. 107-110; Sep. 1992.
Sakas et al.; Preprocessing and volume rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. on Neural Networks; vol. 2.; No. 6; Nov. 1991.
Specht, D.F.; Blind deconvolution of motion blur using LMS inverse filtering; Lockheed Independent Research (unpublished); Jun. 23, 1975.
Specht, D.F.; Enhancements to probabilistic neural networks; Proc. IEEE International Joint Conf. on Neural Networks; Baltimore, MD; Jun. 1992.
Specht, D.F.; GRNN with double clustering; Proc. IEEE International Joint Conf. Neural Networks; Vancouver, Canada; Jul. 16-21, 2006.
Specht, D.F.; Probabilistic neural networks; Pergamon Press; Neural Networks; vol. 3; pp. 109-118; Feb. 1990.
Von Ramm et al.; High-speed ultrasound volumetric imaging-System. 2. Parallel processing and Image display; IEEE Trans. Ultrason., Ferroelect., Freq. Contr.; vol. 38; pp. 109-115; Mar. 1991.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Specht et al.; U.S. Appl. No. 13/773,340 entitled "Determining Material Stiffness Using Multiple Aperture Ultrasound," filed Feb. 21, 2013.
Li et al.; An efficient speckle tracking algorithm for ultrasonic imaging; 24; pp. 215-228; Oct. 1, 2002.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Wikipedia; Curve fitting; 5 pages; retrieved from the internet (http:en.wikipedia.org/wiki/Curve_fitting) Dec. 19, 2010.
Wikipedia; Speed of sound; 17 pages; retrieved from the internet (http:en.wikipedia.org/wiki/Speed_of_sound) Feb. 15, 2011.
Abeysekera et al.; Alignment and calibration of dual ultrasound transducers using a wedge phantom; Ultrasound in Medicine and Biology; 37(2); pp. 271-279; Feb. 2011.
Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb. 28, 2008.
Chen et al.; Maximum-likelihood source localization and unknown sensor location estimation for wideband signals in the near-field; IEEE Transactions on Signal Processing; 50(8); pp. 1843-1854; Aug. 2002.
Chen et al.; Source localization and tracking of a wideband source using a randomly distributed beamforming sensor array; International Journal of High Performance Computing Applications; 16(3); pp. 259-272; Fall 2002.
Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.
Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.
Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.
Hsu et al.; Real-time freehand 3D ultrasound calibration; CUED/F-INFENG/TR 565; Department of Engineering, University of Cambridge, United Kingdom; 14 pages; Sep. 2006.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.

(56) References Cited

OTHER PUBLICATIONS

Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Urban et al; Implementation of vibro-acoustography on a clinical ultrasound system; IEEE Transactions on Ultrasonics, Ferroelectrics, and Frequency Control; 58(6); pp. 1169-1181; Jun. 2011 (Author Manuscript).
Urban et al; Implementation of vibro-acoustography on a clinical ultrasound system; IEEE Ultrasonics Symposium (IUS); pp. 326-329; Oct. 14, 2010.
Wang et al.; Photoacoustic tomography of biological tissues with high cross-section resolution: reconstruction and experiment; Medical Physics; 29(12); pp. 2799-2805; Dec. 2002.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.
Arigovindan et al.; Full motion and flow field recovery from echo doppler data; IEEE Transactions on Medical Imaging; 26(1); pp. 31-45; Jan. 2007.
Capineri et al.; A doppler system for dynamic vector velocity maps; Ultrasound in Medicine & Biology; 28(2); pp. 237-248; Feb. 28, 2002.
Dunmire et al.; A brief history of vector doppler; Medical Imaging 2001; International Society for Optics and Photonics; pp. 200-214; May 30, 2001.
Saad et al.; Computer vision approach for ultrasound doppler angle estimation; Journal of Digital Imaging; 22(6); pp. 681-688; Dec. 1, 2009.
Zang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

\* cited by examiner

SYSTEMS AND METHODS FOR IMPROVING ULTRASOUND IMAGE QUALITY BY APPLYING WEIGHTING FACTORS

CROSS REFERENCES TO RELATED APPLICATIONS

This application claims the benefit of U.S. Provisional Patent Application No. 61/615,735, filed on Mar. 26, 2012, titled "Systems and Methods for Improving Ultrasound Image Quality by Applying Weighting Factors", which is incorporated by reference in its entirety.

This application is related to U.S. Pat. No. 8,007,439, issued Aug. 30, 2011 and titled "Method and Apparatus to Produce Ultrasonic Images Using Multiple Apertures;" U.S. patent application Ser. No. 13/029,907, published as 2011/0201933 and titled "Point Source Transmission and Speed-Of-Sound Correction Using Multiple-Aperture Ultrasound Imaging;" U.S. patent application Ser. No. 12/760,375, filed on Apr. 14, 2010, published as 2010/0262013 and titled "Universal Multiple Aperture Medical Ultrasound Probe;" and U.S. patent application Ser. No. 13/279,110, filed on Oct. 21, 2011, published as 2012/0057428 and titled "Calibration of Ultrasound Probes;" all of which are incorporated herein by reference.

INCORPORATION BY REFERENCE

Unless otherwise specified herein, all patents, publications and patent applications mentioned in this specification are herein incorporated by reference to the same extent as if each individual publication or patent application was specifically and individually indicated to be incorporated by reference.

FIELD

This invention generally relates to ultrasound imaging and more particularly to systems and methods for improving ultrasound imaging quality by applying weighting factors.

BACKGROUND

In conventional ultrasonic imaging, a focused beam of ultrasound energy is transmitted into body tissues to be examined and the returned echoes are detected and plotted to form an image. While ultrasound has been used extensively for diagnostic purposes, conventional ultrasound has been greatly limited by depth of scanning, speckle noise, poor lateral resolution, obscured tissues and other such problems.

In order to insonify body tissues, an ultrasound beam is typically formed and focused either by a phased array or a shaped transducer. Phased array ultrasound is a commonly used method of steering and focusing a narrow ultrasound beam for forming images in medical ultrasonography. A phased array probe has many small ultrasonic transducer elements, each of which can be pulsed individually. By varying the timing of ultrasound pulses (e.g. by pulsing elements one by one in sequence along a row), a pattern of constructive interference is set up that results in a beam directed at a chosen angle. This is known as beam steering. Such a steered ultrasound beam may then be swept through the tissue or object being examined. Data from multiple beams are then combined to make a visual image showing a slice through the object.

Traditionally, the same transducer or array used for transmitting an ultrasound beam is used to detect the returning echoes. This design configuration lies at the heart of one of the most significant limitations in the use of ultrasonic imaging for medical purposes: poor lateral resolution. Theoretically, the lateral resolution could be improved by increasing the width of the aperture of an ultrasonic probe, but practical problems involved with aperture size increase have kept apertures small. Unquestionably, ultrasonic imaging has been very useful even with this limitation, but it could be more effective with better resolution.

Significant improvements have been made in the field of ultrasound imaging with the creation of multiple aperture imaging, examples of which are shown and described in Applicant's prior patents and applications referenced above. Multiple aperture imaging methods and systems allow for ultrasound signals to be both transmitted and received from separate apertures.

SUMMARY OF THE DISCLOSURE

A method of forming an ultrasound image is provided, the method comprising transmitting an unfocused first circular wave front ultrasound signal into a region of interest from a first transmit aperture and receiving echoes of the first circular wave front ultrasound signal at a first receive aperture to form a first image layer, transmitting an unfocused second circular wave front ultrasound signal into a region of interest from a second transmit aperture and receiving echoes of the second circular wave front ultrasound signal at the first receive aperture to form a second image layer, applying a weighting factor to at least one pixel of the first image layer to obtain a modified first image layer, and combining the modified first image layer with the second image layer to form a combined image.

In some embodiments, the method further comprises applying a weighting factor to a least one pixel of the second image layer to obtain a modified second image layer.

In other embodiments, the method further comprises, prior to applying the weighting factor, determining a value of the weighting factor by determining an angle between a point represented by the at least one pixel and the first transmit aperture, and determining the value of weighting factor as a mathematical function of the determined angle.

In one embodiment, the method further comprises, prior to applying the weighting factor, determining a value of the weighting factor by determining an angle between a point represented by the at least one pixel and the first receive aperture, and determining the weighting factor as a mathematical function of the determined angle.

In some embodiments, determining the value of the weighting factor comprises determining whether the angle exceeds a threshold value, selecting a first value for the weighting factor if the angle exceeds the threshold value, and selecting a second value for the weighting factor if the angle does not exceed the threshold value.

In other embodiments, determining the value of the weighting factor comprises determining whether the angle exceeds a threshold value, selecting a first value for the weighting factor if the angle exceeds the threshold value, and selecting a second value for the weighting factor if the angle does not exceed the threshold value.

In one embodiment, the method further comprises, prior to applying the weighting factor, determining a value of the weighting factor by determining a first distance from one of the first or second transmit apertures to a point represented by the at least one pixel, determining a second distance from the point to the first receive aperture, summing the first distance and the second distance to obtain a total path length, and determining the weighting factor as a mathematical function of the total path length.

In some embodiments, applying the weighting factor comprises multiplying the weighting factor by a pixel intensity value of the at least one pixel.

In other embodiments, applying the weighting factor decreases the value of pixels that are identified as likely to contain more than a threshold level of noise.

In one embodiment, the method further comprises transmitting the first circular wave front at a first frequency, and transmitting the second circular wavefront at a second frequency, the first frequency being greater than the second frequency, and applying a weighting factor to at least one pixel in the second image based on the difference between the first frequency and the second frequency.

In some embodiments, the mathematical function is selected from the group consisting of a monotonic function, a linear function, a normal distribution, a parabolic function, a geometric function, an exponential function, a Gaussian distribution, and a Kaiser-Bessel distribution.

In another embodiment, the method comprises, prior to applying the weighting factor, determining a value of the weighting factor by evaluating a quality of a point-spread-function of the first transmit aperture and the first receive aperture, determining that a pixel image obtained using the first transmit aperture and the first receive aperture will improve image quality, and assigning a non-zero positive value to the weighting factor.

In some embodiments, the method also comprises, prior to applying the weighting factor, determining a value of the weighting factor by evaluating a quality of a point-spread-function of the first transmit aperture and the first receive aperture, determining that a pixel image obtained using the first transmit aperture and the first receive aperture will degrade image quality, and assigning a value of zero to the weighting factor.

In another embodiment, the method further comprises changing an image window by zooming or panning to a different portion of the region of interest, determining a new weighting factor value based on the changed image window.

A method of identifying transmit elements not blocked by an obstacle is also provided, the method comprising transmitting an unfocused first circular wave front ultrasound signal from a first transmit aperture and receiving echoes of the first circular wave front ultrasound signal at a first receive aperture, determining whether deep echo returns from within the region of interest are received by identifying if a time delay associated with the received echoes exceeds a threshold value, and identifying the first transmit aperture as being clear of an obstacle if deep echo returns are received.

Another method of identifying transducer elements blocked by an obstacle is provided, the method comprising transmitting an unfocused first circular wave front ultrasound signal from a first transmit aperture and receiving echoes of the first circular wave front ultrasound signal at a first receive aperture, determining whether strong shallow echo returns are received by identifying a plurality of echo returns with intensity values greater than a threshold intensity and with time delays less than a threshold time delay, and identifying the first transmit aperture as being blocked by an obstacle if strong shallow echo returns are received.

An ultrasound imaging system is also provided comprising an ultrasound transmitter configured to transmit unfocused ultrasound signals into a region of interest, an ultrasound receiver configured to receive ultrasound echo signals returned by reflectors in the region of interest, a beamforming module configured to determine positions of the reflectors within the region of interest for displaying images of the reflectors on a display, first user-adjustable controls configured to select a designated aperture from a plurality of transmit apertures and receive apertures of the ultrasound transmitter and ultrasound receiver, and second user-adjustable controls configured to increase or decrease a speed-of-sound value used by the beamforming module to determine the positions of reflectors detected with the designated aperture.

In one embodiment, the designated aperture is a transmit aperture. In another embodiment, the designated aperture is a receive aperture.

Another ultrasound imaging system is provided, comprising a first transmit aperture configured to transmit first and second unfocused circular wave front ultrasound signals into a region of interest, a first receive aperture configured to receive echoes of the first and second circular wave front ultrasound signals, and a controller configured to form a first image layer from received echoes of the first circular wave front ultrasound signal, and configured to form a second image layer from received echoes of the second circular wave front ultrasound signal, the controller being further configured to apply a weighting factor to at least one pixel of the first image layer to obtain a modified first image layer, and to combine the modified first image layer with the second image layer to form a combined image.

In some embodiments, the controller is configured to apply a weighting factor to a least one pixel of the second image layer to obtain a modified second image layer.

In other embodiments, the controller is configured to determine a value of the weighting factor by determining an angle between a point represented by the at least one pixel and the first transmit aperture, the controller being further configured to determine the value of weighting factor as a mathematical function of the determined angle.

In some embodiments, the controller is configured to determine a value of the weighting factor by determining an angle between a point represented by the at least one pixel and the first receive aperture, the controller being further configured to determine the weighting factor as a mathematical function of the determined angle.

In one embodiment, determining the value of the weighting factor comprises determining whether the angle exceeds a threshold value, selecting a first value for the weighting factor if the angle exceeds the threshold value, and selecting a second value for the weighting factor if the angle does not exceed the threshold value.

In another embodiment, determining the value of the weighting factor comprises determining whether the angle exceeds a threshold value, selecting a first value for the weighting factor if the angle exceeds the threshold value, and selecting a second value for the weighting factor if the angle does not exceed the threshold value.

In some embodiments, the controller is configured to determine a value of the weighting factor by determining a first distance from one of the first or second transmit apertures to a point represented by the at least one pixel, determining a second distance from the point to the first receive aperture, summing the first distance and the second distance to obtain a total path length, and determining the weighting factor as a mathematical function of the total path length.

In one embodiment, applying the weighting factor comprises multiplying the weighting factor by a pixel intensity value of the at least one pixel.

In another embodiment, applying the weighting factor decreases the value of pixels that are identified as likely to contain more than a threshold level of noise.

In some embodiments, the first transmit aperture is configured to transmit the first circular wave front at a first frequency and the second circular wavefront at a second frequency, the first frequency being greater than the second frequency, and the controller is configured to apply a weighting factor to at least one pixel in the second image based on the difference between the first frequency and the second frequency.

In another embodiment, the mathematical function is selected from the group consisting of a monotonic function, a linear function, a normal distribution, a parabolic function, a geometric function, an exponential function, a Gaussian distribution, and a Kaiser-Bessel distribution.

In another embodiment, the controller, prior to applying the weighting factor, is configured to determine a value of the weighting factor by evaluating a quality of a point-spread-function of the first transmit aperture and the first receive aperture, the controller being configured to determine that a pixel image obtained using the first transmit aperture and the first receive aperture will improve image quality, the controller being further configured to assign a non-zero positive value to the weighting factor.

In some embodiments, the controller is configured to determine a value of the weighting factor by evaluating a quality of a point-spread-function of the first transmit aperture and the first receive aperture, the controller being configured to determine that a pixel image obtained using the first transmit aperture and the first receive aperture will degrade image quality, the controller being further configured to assign a value of zero to the weighting factor.

In another embodiment, the controller is further configured to change an image window by zooming or panning to a different portion of the region of interest, the controller further being configured to determine a new weighting factor value based on the changed image window.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The various embodiments will be described in detail with reference to the accompanying drawings. References made to particular examples and implementations are for illustrative purposes, and are not intended to limit the scope of the invention or the claims.

The present disclosure provides systems and methods for improving the quality of ultrasound images made up of a combination of multiple sub-images by assigning relatively more weight to sub-image information that is more likely to improve overall quality of a combined image. In some cases, this may be achieved by amplifying the effect of higher quality sub-image information. In other embodiments, image optimization may be achieved by reducing the effect of lower quality sub-image information. In some embodiments, such information may be determined from a known location of a specific transducer element relative to a specific region of an image. In some embodiments, any given pixel (or other discrete region of an image) may be formed by combining received echo data in a manner that gives more weight to data that is likely to improve image quality, and/or discounting or ignoring data that is likely to detract from image quality (e.g., by introducing noise or by increasing point spread). Details of systems and methods for achieving such improvements are provided herein.

Although the various embodiments are described herein with reference to ultrasound imaging of various anatomic structures, it will be understood that many of the methods and devices shown and described herein may also be used in other applications, such as imaging and evaluating non-anatomic structures and objects.

Figure 1A:
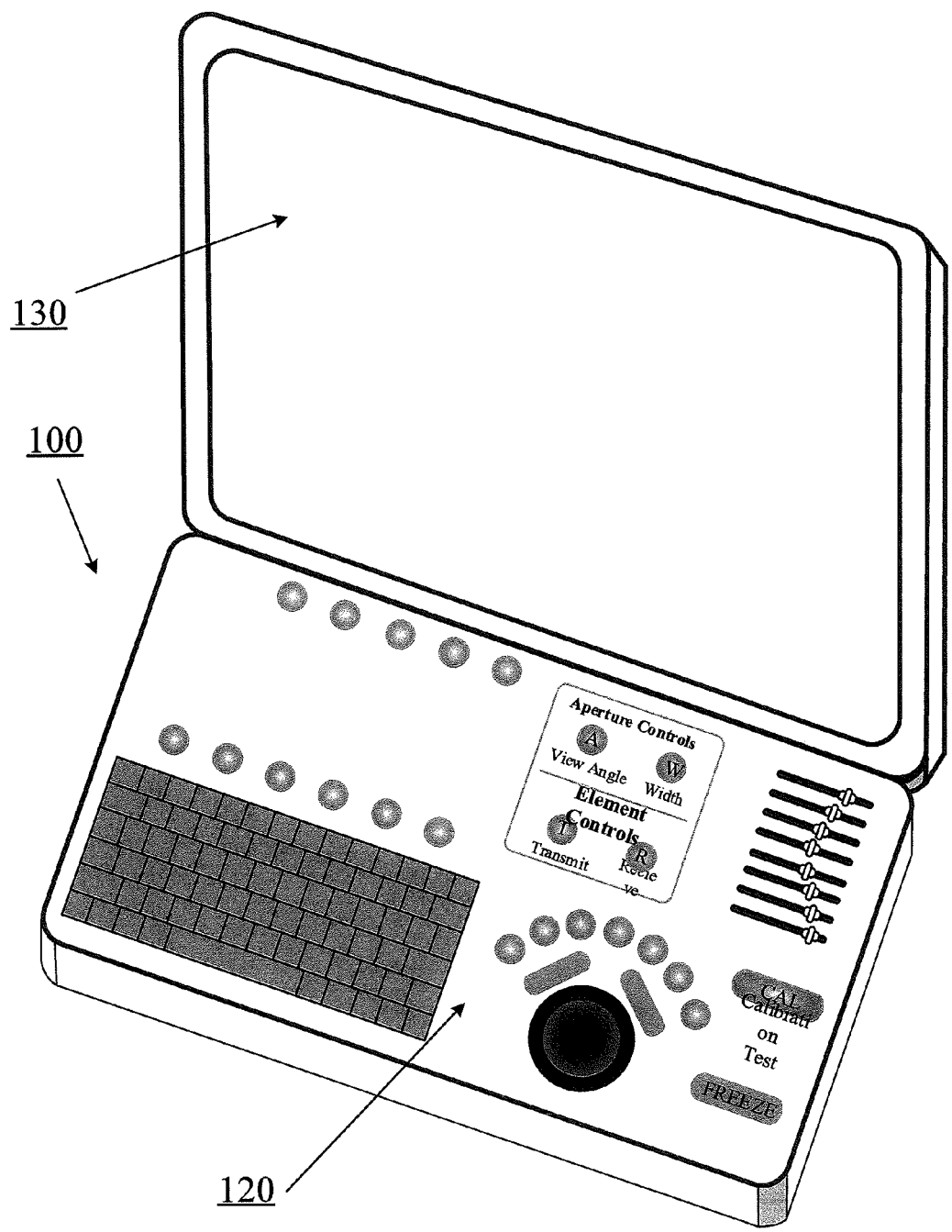
FIG. 1A is a perspective view illustration of an embodiment of a multiple aperture ultrasound imaging control system.

A multiple aperture ultrasound system may include a control unit containing electronics, hardware, software, and user interface components for controlling a multiple aperture imaging process. FIG. 1A illustrates an example of a multiple aperture ultrasound imaging control system 100 which has a control panel 120 and a display screen 130. The imaging control system also contains electronic hardware and software configured to transmit, receive and process ultrasound signals using a multiple aperture ultrasound imaging (MAUI) probe. Such hardware and software is generically referred to herein as MAUI electronics. In some embodiments, a MAUI control system may also include a calibration unit (not shown). In such embodiments, a calibration unit may be electronically connected to the MAUI electronics by any wired or wireless communications system. In further embodiments, the electronics controlling a calibration system, including electronics controlling a probe during calibration, may be entirely independent (physically and/or electronically) of the electronics used for controlling an ultrasound imaging process. Some examples of suitable calibration systems are shown and described in U.S. patent application Ser. No. 13/279,110 (publication no. 2012/0057428), which is incorporated herein by reference. In some embodiments, the MAUI electronics may include only hardware and software sufficient to perform a portion of an imaging process. For example, in some embodiments the system 100 may include only controls and electronics for capturing image data, while hardware, software, electronics and controls for processing and displaying an image may be external to the system 100.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micro machined ultrasound transducers (CMUT) or any other transducing device capable of converting ultrasound waves to and from electrical signals.

Transducers are often configured in arrays of multiple individual transducer elements. As used herein, the terms "transducer array" or "array" generally refers to a collection of transducer elements mounted to a common backing plate. Such arrays may have one dimension (1D), two dimensions (2D), 1.X dimensions (1.XD) or three dimensions (3D). Other dimensioned arrays as understood by those skilled in the art may also be used. Annular arrays, such as concentric circular arrays and elliptical arrays may also be used. An element of a transducer array may be the smallest discretely functional component of an array. For example, in the case of an array of piezoelectric transducer elements, each element may be a single piezoelectric crystal or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Transmitted ultrasound signals may be focused in a particular direction, or may be unfocused, transmitting in all directions or a wide range of directions. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a single transducer element or a group of transducer elements that are collectively managed as a common group by imaging control electronics. For example, in some embodiments an aperture may be a grouping of elements which may be physically separate and distinct from elements of an adjacent aperture. However, adjacent apertures need not necessarily be physically separate or distinct. Conversely, a single aperture may include elements of two or more physically separate or distinct transducer arrays. For example or distinct groups of transducer elements (e.g., a "left aperture" may be constructed from a left array, plus the left half of a physically distinct center array, while a "right aperture" may be constructed from a right array, plus the right half of a physically distinct center array).

It should be noted that the terms "receive aperture," "insonifying aperture," and/or "transmit aperture" are used herein to mean an individual element, a group of elements within an array, or even entire arrays, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture may all have the same dimensions. In the case of a multiple aperture imaging arrangement, the dimensions of the total aperture includes the sum of the dimensions of all send and receive apertures.

In some embodiments, two apertures may be located adjacent to one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Elements and arrays described herein may also be multi-function. That is, the designation of transducer elements or arrays as transmitters in one instance does not preclude their immediate re-designation as receivers in the next instance. Moreover, embodiments of the control system herein include the capabilities for making such designations electronically based on user inputs, pre-set scan or resolution criteria, or other automatically determined criteria.

As used herein the term "point source transmission" may refer to an introduction of transmitted ultrasound energy into a medium from single spatial location. This may be accomplished using a single ultrasound transducer element or combination of adjacent transducer elements transmitting together as a single transmit aperture. A single transmission from a point source transmit aperture approximates a uniform spherical wave front, or in the case of imaging a 2D slice, a uniform circular wave front within the 2D slice. In some cases, a single transmission of a circular, semi-circular, spherical or semi-spherical wave front from a point source transmit aperture may be referred to herein as an "unfocused circular wave front ultrasound signal", a "ping", or a "point source pulse."

Point source transmission differs in its spatial characteristics from a "phased array transmission" which focuses energy in a particular direction from the transducer element array. A point source pulse (ping) may be transmitted so as to generate a circular wavefront in the scanning plane. Images may then be reconstructed from echoes assuming that the wavefronts emitted from point source transmitters are physically circular in the region of interest. In actuality, the wavefront may also have some penetration in the dimension normal to the scanning plane (i.e., some energy may essentially "leak" into the dimension perpendicular to the desired two-dimensional scanning plane, reducing the effective imaging reach). Additionally, the "circular" wavefront may actually be limited to a semicircle or a fraction of a circle less than 180 degrees ahead of the front face of the transducer according to the unique off-axis properties of the transducing material. Phased array transmission, on the other hand, manipulates the transmission phase of a group of transducer elements in sequence so as to strengthen or steer an insonifying wave to a specific region of interest (mathematically and physically, this is done by means of constructive and destructive interference along multiple overlapping wavefronts). Phased array transmission also suffers the same third-dimension energy leakage (off plane) as point source transmission. A short duration phased array transmission may be referred to herein as a "phased array pulse."

Figure 1B:
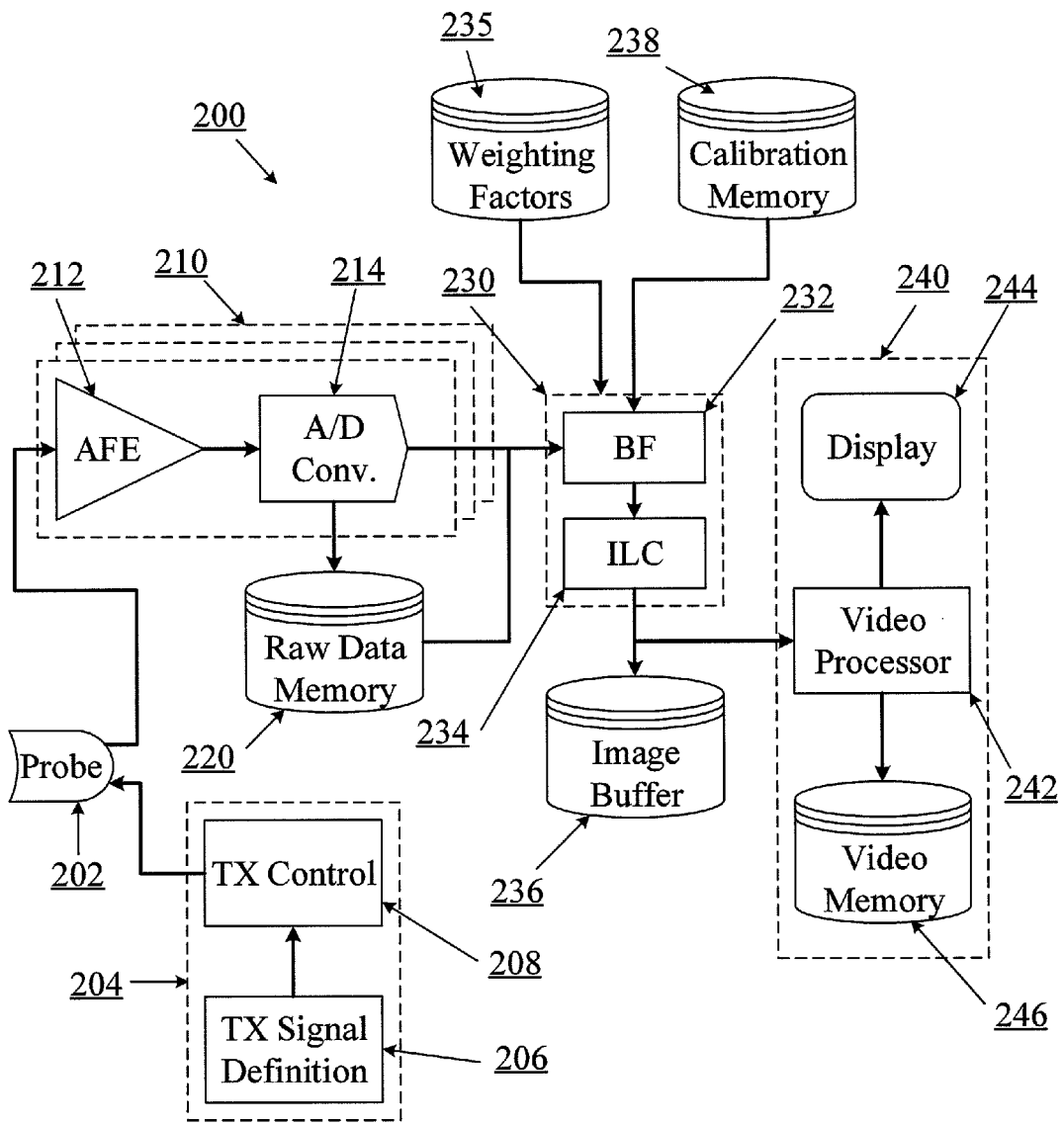
FIG. 1B is a block diagram illustrating an embodiment of some components of an imaging system that may be used in combination with the systems and methods herein.

The block diagram of FIG. 1B illustrates components of an ultrasound imaging system 200 that may be used in combination with various embodiments of systems and methods as described herein. The system 200 of FIG. 1B may include several subsystems: a transmit control subsystem 204, a probe subsystem 202, a receive subsystem 210, an image generation subsystem 230, and a video subsystem 240. In various embodiments, the system 200 may also include one or more memory devices for containing various data for use during one or more ultrasound imaging steps. Such memory devices may include a raw echo data memory 220, a weighting factor memory 235, a calibration data memory 238, an image buffer 236 and/or a video memory 246. In various embodiments all data (including software and/or firmware code for executing any other process) may be stored on a single memory device. Alternatively, separate memory devices may be used for one or more data types. Further, any of the modules or components represented in FIG. 2B may be implemented using any suitable combination of electronic hardware, firmware and/or software.

The transmission of ultrasound signals from elements of the probe 202 may be controlled by a transmit control subsystem 204. In some embodiments, the transmit control subsystem 204 may include any combination of analog and digital components for controlling transducer elements of the probe 202 to transmit un-focused ultrasound pings at desired frequencies and intervals from selected transmit apertures according to a desired imaging algorithm. In some embodiments a transmit control system 204 may be configured to transmit ultrasound pings at a range of ultrasound frequencies. In some (though not all) embodiments, the transmit control subsystem may also be configured to control the probe in a phased array mode, transmitting focused (i.e. transmit beamformed) ultrasound scanline beams.

In some embodiments, a transmit control sub-system 204 may include a transmit signal definition module 206 and a transmit element control module 208. The transmit signal definition module 206 may include suitable combinations of hardware, firmware and/or software configured to define desired characteristics of a signal to be transmitted by an ultrasound probe. For example, the transmit signal definition module 206 may establish (e.g., based on user inputs or on pre-determined factors) characteristics of an ultrasound signal to be transmitted such as a pulse start time, pulse length (duration), ultrasound frequency, pulse power, pulse shape, pulse direction (if any), pulse amplitude, transmit aperture location, or any other characteristics.

The transmit element control module 208 may then take information about the desired transmit pulse and determine appropriate electrical signals to be sent to appropriate transducer elements in order to produce the designated ultrasound signal. In various embodiments, the signal definition module 206 and the transmit element control module 208 may comprise separate electronic components, or may include portions of one or more common components.

Upon receiving echoes of transmitted signals from a region of interest, the probe elements may generate time-varying electric signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214. In some embodiments, each channel of the receive subsystem 210 may also include digital filters and data conditioners (not shown) after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some pre-determined sampling rate. Unlike most ultrasound systems, some embodiments of the ultrasound imaging system of FIG. 3 may then store digital data representing the timing, phase, magnitude and/or the frequency of ultrasound echo signals received by each individual receive element in a raw data memory device 220 before performing any further receive beamforming, filtering, image layer combining or other image processing.

In order to convert the captured digital samples into an image, the data may be retrieved from the raw data memory 220 by an image generation subsystem 230. As shown, the image generation subsystem 230 may include a beamforming block 232 and an image layer combining ("ILC") block 234. In some embodiments, a beamformer 232 may be in communication with a calibration memory 238 that contains probe calibration data. Probe calibration data may include information about the precise position, operational quality, and/or other information about individual probe transducer elements. The calibration memory 238 may be physically located within the probe, within the imaging system, or in location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g. as referred to in the art as a "cine loop".

In some embodiments, the AFE 212 may be configured to perform various amplification and filtering processes to a received analog signal before passing the analog signal to an analog-to-digital conversion device. For example, an AFE 212 may include amplifiers such as a low noise amplifier (LNA), a variable gain amplifier (VGA), a bandpass filter, and/or other amplification or filtering devices. In some embodiments, an AFE device 212 may be configured to begin passing an analog signal to an ADC 214 upon receiving a trigger signal. In other embodiments, an AFE device can be "free running", continuously passing an analog signal to an ADC.

In some embodiments, each analog-to-digital converter 214 may generally include any device configured to sample a received analog signal at some consistent, pre-determined sampling rate. For example, in some embodiments, an analog-to-digital converter may be configured to record digital samples of a time-varying analog signal at 25 MHz, which is 25 million samples per second or one sample every 40 nanoseconds. Thus, data sampled by an ADC may simply include a list of data points, each of which may correspond to a signal value at a particular instant. In some embodiments, an ADC 214 may be configured to begin digitally sampling an analog signal upon receiving a trigger signal. In other embodiments, an ADC device can be "free running", continuously sampling a received analog signal.

In some embodiments, the raw data memory device 220 may include any suitable volatile or non-volatile digital memory storage device. In some embodiments, the raw data memory 220 may also comprise communication electronics for transmitting raw digital ultrasound data to an external device over a wired or wireless network. In such cases, the transmitted raw echo data may be stored on the external device in any desired format. In other embodiments, the raw data memory 220 may include a combination of volatile memory, non-volatile memory and communication electronics.

In some embodiments, the raw data memory device 220 may comprise a temporary (volatile or non-volatile) memory section, and a long-term non-volatile memory section. In an example of such embodiments, the temporary memory may act as a buffer between the ADC 214 and the beamformer 232 in cases where the beamformer 232 may be unable to operate fast enough to accommodate data at the full rate from the ADC 214. In some embodiments, a long-term non-volatile memory device may be configured to receive data from a temporary memory device or directly from the ADC 214. Such a long-term memory device may be configured to store a quantity of raw echo data for subsequent processing, analysis or transmission to an external device.

In some embodiments, the beamforming block 232 and the image layer combining block 234 may each include any digital signal processing and/or computing components configured to perform the specified processes (e.g., as described below). For example, in various embodiments the beamforming 232 and image layer combining 234 may be performed by software running on a single GPU, on multiple GPUs, on one or more CPUs, on combinations of CPUs & GPUs, on single or multiple accelerator cards or modules, on a distributed processing system, or a clustered processing system. Alternatively, these or other processes may be performed by firmware running on a FPGA architecture or one or more dedicated ASIC devices.

In some embodiments, the video processor 242 may include any video processing hardware, firmware and software components that may be configured to assemble image frames into a video stream for display and/or storage.

A weighting factor memory device may contain data defining weighting factor values to be applied during beamforming, image layer combining, image processing, or any other stage of image formation as desired. Examples of various types of weighting factors are provided below.

Figure 2:
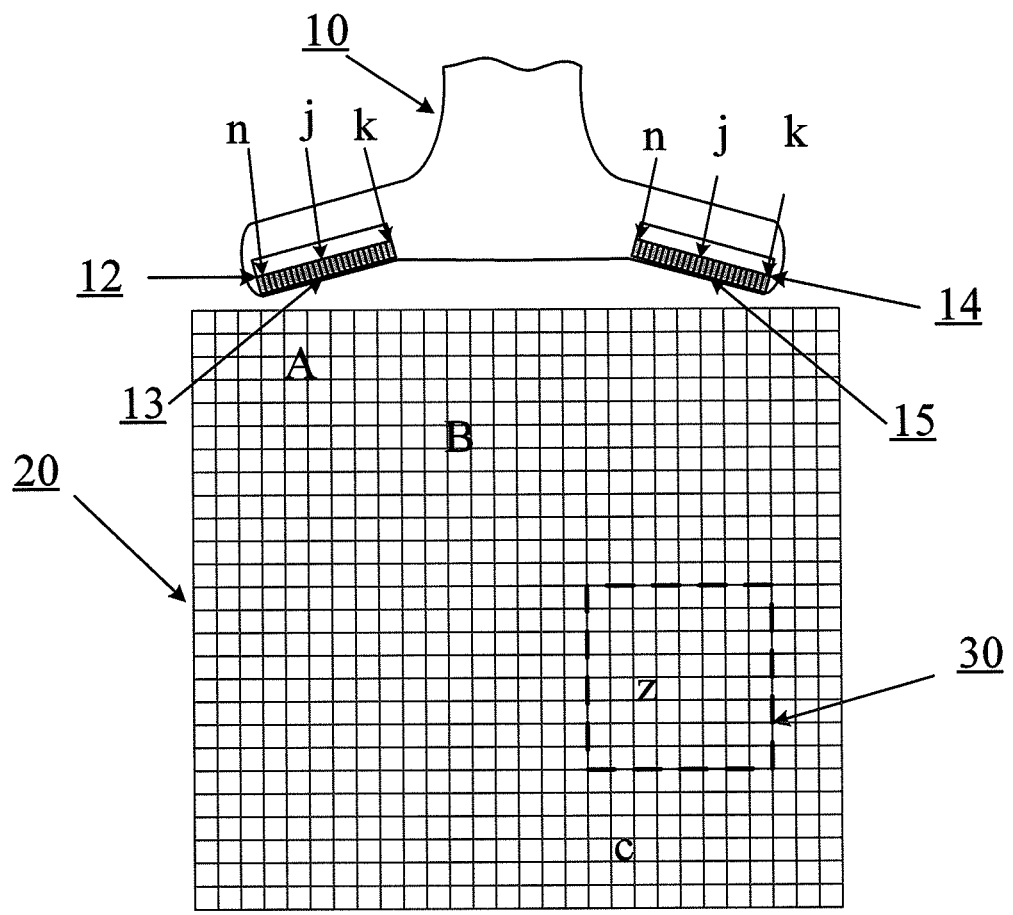
FIG. 2 is a schematic illustration of a multiple aperture ultrasound imaging probe with two transducer arrays and a grid of points/pixels to be imaged.

FIG. 2 illustrates an embodiment of a multiple aperture ultrasound imaging probe 10 and a region of interest 20 to be imaged represented as a grid. The probe 10 is shown with a left transducer array 12 which includes three transmit apertures labeled 'n,' 'j,' and 'k' (which may be referred to herein by short-hand designations Ln, Lj and Lk). A right transducer array 14 also includes three transmit apertures 'n,' 'j,' and 'k' (which may be referred to herein by short-hand designations Rn, Rj and Rk). Some or all of the elements of the left transducer array 12 may also be designated as a left receive aperture 13. Similarly, some or all of the elements of the right transducer array 14 may be designated as a right receive aperture 15.

Figure 3:
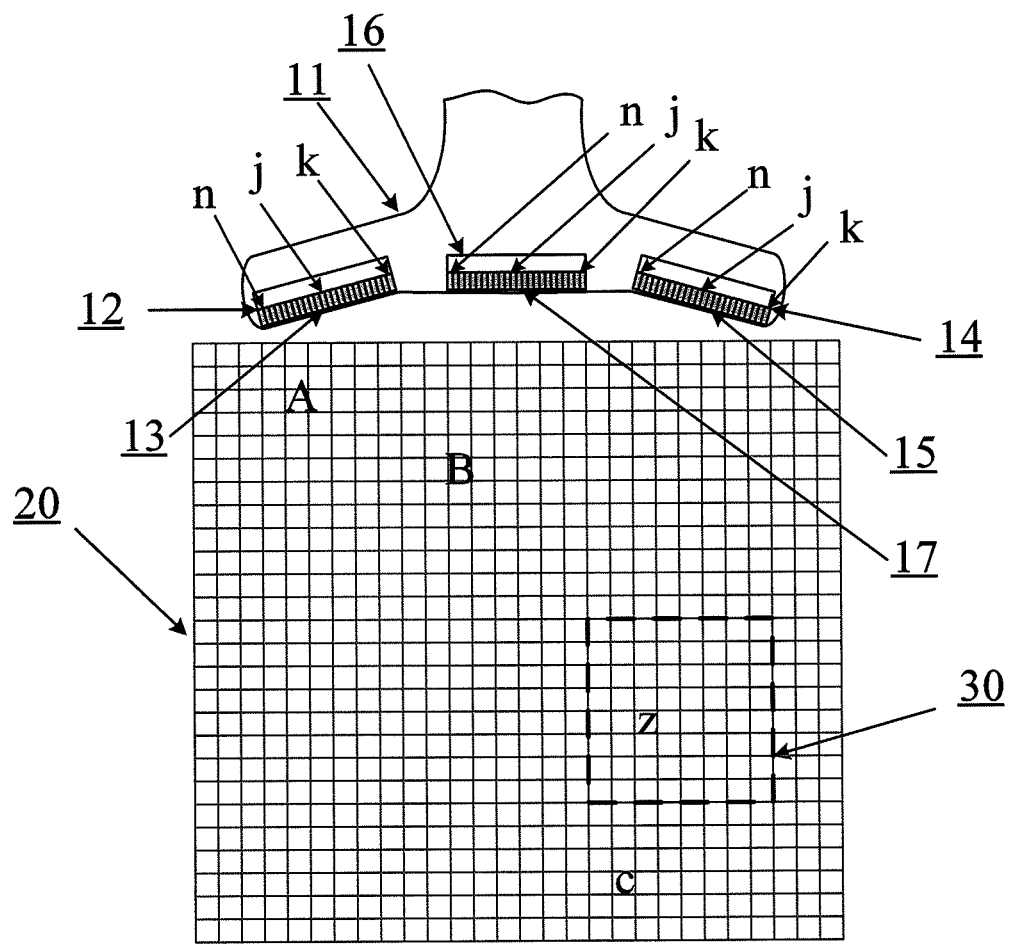
FIG. 3 is a schematic illustration of a multiple aperture ultrasound imaging probe with three transducer arrays and a grid of points/pixels to be imaged.

FIG. 3 illustrates an embodiment of a three-array multiple aperture ultrasound imaging probe 11. In addition to the left and right arrays of the two-array probe, the three-array probe includes a center transducer array 16, which includes three transmit apertures labeled 'n,' 'j,' and 'k' (which may be referred to herein by short-hand designations Cn, Cj and Ck). Some or all of the elements of the center transducer array 16 may also be designated as a center receive aperture 17. In other embodiments, any other multiple aperture probe construction may also be used with the systems and methods described herein. For example, Applicant's prior applications describe several alternative probe constructions, such as probes with four, five or more arrays, probes with one or more adjustable arrays, probes with one or more large arrays that may be electronically sub-divided into any number of apertures, and single-aperture probes, any of which (or others) may be used in connection with the systems and methods described herein.

In some embodiments, the width of a receive aperture may be limited by the assumption that the average speed of sound is approximately the same for every path from a scatterer to each element of the receive aperture. Given a sufficiently narrow receive aperture this simplifying assumption is acceptable. However, as the receive aperture width increases, a tipping point is reached (referred to herein as the "maximum coherent aperture width" or "maximum coherence width"), beyond which the echo return paths will necessarily pass though different types of tissue having intrinsically different speeds of sound. When this difference results in receive wavefront phase shifts approaching or exceeding 180 degrees, additional receive elements extended beyond the maximum coherent receive aperture width will actually degrade the image rather than improve it.

Therefore, in order to realize the inherent benefits of a wide probe with a total aperture width far greater than the maximum coherent aperture width, the full probe width may be physically or logically divided into multiple apertures, each of which may be limited to an effective width less than or equal to the maximum coherent aperture width, and thus small enough to avoid phase cancellation of received signals. The maximum coherence width can be different for different patients and for different probe positions on the same patient. In some embodiments, a compromise width may be determined for a given probe system. In other embodiments, a multiple aperture ultrasound imaging control system may be configured with a dynamic algorithm to subdivide the available elements in multiple apertures into groups that are small enough to avoid significant image-degrading phase cancellation.

In some embodiments, it may be difficult or impossible to meet additional design constraints while grouping elements into apertures with a width less than the maximum coherence width. For example, if material is too heterogeneous over very small areas, it may be impractical to form apertures small enough to be less than the maximum coherence width. Similarly, if a system is designed to image a very small target at a substantial depth, an aperture with a width greater than the maximum coherence width may be needed. In such cases, a receive aperture with a width greater than the maximum coherence width can be accommodated by making additional adjustments or corrections to account for differences in the speed-of-sound along different paths. Some examples of such speed-of-sound adjustments are provided here, while additional examples are provided in US Patent Application Publication 2010/0201933, titled "Universal Multiple Aperture Medical Ultrasound Probe." In some embodiments, because the maximum coherence width is ultimately variable from patient-to-patient and from location-to-location even for a single patient, it may be desirable to provide a user-interface adjustment configured to allow a user to selectively increase or decrease a maximum coherence width during an imaging session, or during post-processing of stored raw echo data. The adjusted maximum coherence width may be applied by correspondingly increasing or decreasing the size of receive apertures (i.e., transducer element groups) to be used during beamforming.

Image Layer Combining

In some embodiments, multiple aperture imaging using a series of transmit pings may operate by transmitting a point-source ping from a first transmit aperture and receiving echoes with elements of two or more receive apertures. A complete image may be formed by triangulating the position of scatterers based on delay times between ping transmission and echo reception. As a result, a complete image may be formed by a controller or control system from data received at each receive aperture from echoes of each transmit ping. Images obtained from different unique combinations of a ping and a receive aperture may be referred to herein as image layers. Multiple image layers may be combined to improve the overall quality of a final combined image. Thus, in some embodiments the total number of image layers generated can be the product of the number of receive apertures and the number of transmit apertures (where a "transmit aperture" can be a single transmit element or a group of transmit elements).

For example, in some embodiments, a single time domain frame may be formed by combining image layers formed from echoes at two or more receive apertures from a single transmit ping. In other embodiments, a single time domain frame may be formed by combining image layers formed from echoes at one or more receive apertures from two or more transmit pings. In some such embodiments, the multiple transmit pings may originate from different transmit apertures.

For example, in one embodiment with reference to FIG. 2, a first image layer (representing all points in the grid 20, or only a section of the grid 20 if panning/zooming to a particular target of interest 30) may be formed by transmitting a first ping from a first transmit aperture Ln and receiving echoes of the first ping at a left receive aperture 13. A second image layer may be formed from echoes of the first ping received at the right receive aperture 15. Third and fourth image layers may be formed by transmitting a second ping from a second transmit aperture Lj and receiving echoes of the second ping at the left receive aperture 13 and the right receive aperture 15. In some embodiments, all four image layers may then be combined to form a single time domain image frame. In other embodiments, a single time domain image frame may be obtained from echoes received at any number of receive apertures from any number of pings transmit by any number of transmit apertures. Time domain image frames may then be displayed sequentially on a display screen as a continuous moving image. Still images may also be formed by combining image layers using any of the above techniques.

Display screens and the images displayed on them may generally be divided into a grid of pixels. In some cases, a pixel is the smallest individually controllable area of a display screen. Relationships between image pixels and display pixels are generally well understood in the art, and will not be described here. For the purposes of the present description, the square cells of the grids 20 shown in the figures will be referred to as pixels. In many of the embodiments herein, groups of pixels may be treated together as a common group. Thus, the use of the term "pixel" is not intended to be limited to any particular size, but is used as a convenient term for describing a discrete section of an image.

In a monochrome display each pixel is assigned only one value: "intensity", which is a scalar value that defines how much light the pixel should display. In a color display, in addition to an intensity value, each pixel may be assigned multiple color component values, such as red, green, and blue; or cyan, magenta, yellow, and black. The following description will primarily refer to applying weighting factors against various contributions to a pixel's intensity from multiple sources. However, in some embodiments some or all color values may also be weighted using the same or related techniques.

With a multiple aperture probe using a point-source transmission imaging technique, each image pixel may be assembled by beamforming received echo data on a per-receive element basis, combining information from echoes received at each of the multiple receive elements within each of the multiple receive apertures (the echoes having resulted from pings transmitted from each of the multiple transmitters within each of the multiple transmit apertures). In some embodiments of multiple aperture imaging with point-source transmission, receive beamforming comprises forming a pixel of a reconstructed image by summing time-delayed echo returns on receive transducer elements from a scatterer in the object being examined. The time delays of a scatterer's echoes recorded at each receiver are a function of the unique geometry of the probe elements, combined with an assumed value for the speed of sound through the medium being imaged. An important consideration is whether the summation should be coherent (phase sensitive) or incoherent (summing signal magnitudes only and disregarding phase information). Further details of ping-based beamforming are described in Applicants' patent application Ser. No. 13/029,907 which is incorporated herein by reference.

Summation or averaging of image layers resulting from multiple transmit pings may be accomplished either by coherent addition, incoherent addition, or a combination of the two. Coherent addition (incorporating both phase and magnitude information during image layer summation) tends to maximize lateral resolution, whereas incoherent addition (summing magnitudes only and omitting phase information) tends to average out speckle noise and minimize the effects of image layer alignment errors that may be caused by minor variations in the speed of sound through the imaged medium. Speckle noise is reduced through incoherent summing because each image layer will tend to develop its own independent speckle pattern, and summing the patterns incoherently has the effect of averaging out these speckle patterns. Alternatively, if the patterns are added coherently, they reinforce each other and only one strong speckle pattern results. Incoherent addition may be thought of as akin to instantaneous compound imaging, which has long been known as a means to suppress speckle noise.

Variations in the speed of sound may be tolerated by incoherent addition as follows: Summing two pixels coherently with a speed-of-sound variation resulting in only half a wavelength's delay (e.g., approximately 0.25 mm for a 3 MHz probe) results in destructive phase cancellation, which causes significant image data loss; if the pixels are added incoherently, the same or even greater delay causes only an insignificant spatial distortion in the image layer and no loss of image data. The incoherent addition of such image layers may result in some smoothing of the final image (in some embodiments, such smoothing may be added intentionally to make the image more readable).

Image layer combining may be described in terms of three image layer levels for which the determination of coherent vs. incoherent summing can be made. These three cases include first-level image layers, second-level image layers and third-level image layers. (1) A first-level image layer may be formed from echoes received at a single receive aperture resulting from a single ping from a single transmit aperture. For a unique combination of a single ping and a single receive aperture, the delayed echoes received by all the receive elements in the receive aperture may be summed to obtain a first-level image layer. (2) Multiple first-level image layers resulting from echoes of multiple transmit pings (from the same or different transmit apertures) received at a single receive aperture can be summed together to produce a second-level image layer. Second-level image layers may be further processed to improve alignment or other image characteristics. (3) Third-level images may be obtained by combining second-level image layers formed with data from multiple receive apertures. In some embodiments, third-level images may be displayed as sequential time-domain frames to form a moving image.

At all three image layer levels, coherent addition can lead to maximum lateral resolution of a multiple aperture system if the geometry of the probe elements is known to a desired degree of precision and the assumption of a constant speed of sound across all paths is valid. Likewise, at all image layer levels, incoherent addition leads to the best averaging out of speckle noise and tolerance of minor variations in speed of sound through the imaged medium.

In some embodiments, coherent addition can be used to combine image layers resulting from apertures for which phase cancellation is not likely to be a problem, and incoherent addition can then be used where phase cancellation would be more likely to present a problem, such as when combining images formed from echoes received at different receive apertures separated by a distance exceeding some threshold.

In some embodiments, all first-level images may be formed by using coherent addition assuming the receive apertures used were chosen to have a width less than the maximum coherent aperture width. For second and third level image layers, many combinations of coherent and incoherent summation are possible. For example, in some embodiments, second-level image layers may be formed by coherently summing contributing first-level image layers, while third-level image layers may be formed by incoherent summing of the contributing second-level image layers.

Speckle Preset Control

In other embodiments, it may be desirable to combine image layers through any of a wide variety of algorithms using combinations of coherent and incoherent summation. In some embodiments, an imaging control system may be configured to store a plurality of selectable pre-programmed summation algorithms that may be designed for specific imaging applications. In some embodiments, stored summation algorithms may be manually selectable such as by operating a manual user interface control. Alternatively, stored summation algorithms may be automatically selectable based on other data or information available to the control system.

For example, in some embodiments an alternative algorithm may comprise forming all second-level and third-level image layers by coherent addition. In another embodiment, all second-level and/or third-level image layers may be formed by incoherent addition. In further embodiments, only selected combinations of second-level images may be combined coherently or incoherently to form third-level images. In other embodiments, only selected combinations of first-level image layers may be combined coherently to form second-level image layers.

In some embodiments, a first-level image layer may also be formed by summing in-phase and quadrature echo data (i.e. summing each echo with an echo ¼ wavelength delayed) for each receive-aperture element. In most embodiments, echoes received by elements of a single receive aperture are typically combined coherently. In some embodiments, the number of receive apertures and/or the size of each receive aperture may be changed in order to maximize some desired combination of image quality metrics such as lateral resolution, speed-of-sound variation tolerance, speckle noise reduction, etc. In some embodiments, such alternative arrangements may be selectable by a user. In other embodiments, such arrangements may be automatically selected or developed by an imaging system.

Once an image layer is formed by incoherent summation, any phase information for that image layer is lost. Thus, any subsequent image layers using an image layer formed by incoherent summation will themselves necessarily be incoherently combined. Thus, in some embodiments, phase information may be retained for as long as desired in an image-layer combining process.

Speed of Sound Control

As discussed above, a speed-of-sound value is typically assumed during beamforming in order to determine the location of ROI points and corresponding pixels based on time delays between a transmit time and a receive time. In soft human tissue, the speed of sound is typically assumed to be about 1540 m/s. However, the speed of sound is known to vary by as much as 10% or more among patients and among different types of soft tissue within a single patient. Variation between an assumed speed-of-sound and an actual value for a particular scatterer path may cause errors during beamforming, which may cause a blurring or spatial displacement effect in an image. Therefore, in some embodiments a multiple aperture ultrasound imaging system may be configured to allow for automatic and/or manual adjustment of an assumed speed of sound value for some or all scatterer paths.

In some embodiments, a multiple aperture imaging system may include a "coarse" speed-of-sound adjustment that increases or decreases an assumed value of speed-of-sound used in beamforming for all scatterer paths (i.e. for all combinations of transmit aperture and receive aperture). In some cases, such an adjustment may also be provided for single-aperture ultrasound imaging systems. A coarse speed-of-sound adjustment may be manual (e.g., a dial, slider or any other physical or virtual user interface device) to allow a sonographer or other user to directly increase or decrease an assumed speed-of-sound value until the system produces a result acceptable to the user. In other embodiments, a "coarse" speed of sound adjustment may be controlled automatically by an imaging control system. Thus, a coarse speed-of-sound adjustment may apply a single adjustment to all image layers.

Various embodiments of "fine" speed-of-sound adjustments may also be provided. In some embodiments, a fine speed-of-sound adjustment may be configured to adjust an assumed speed of sound value for a single receive aperture. In other embodiments, a fine speed-of-sound adjustment may be configured to adjust an assumed speed of sound value for a single transmit aperture. In further embodiments, a fine speed-of-sound adjustment may be configured to adjust an assumed speed of sound value for one or more specific combinations of transmit aperture and receive aperture. Thus, fine speed-of-sound controls may be configured to effectively apply adjustments to specific first-level or second-level image layers. As with coarse speed-of-sound adjustments, fine speed-of-sound adjustments may be manual, automatic or a combination of the two.

In some embodiments, a coarse speed-of-sound adjustment may be made manually by a user, and fine speed-of-sound adjustments may be made automatically by the ultrasound imaging control system. In other embodiments, both coarse and fine speed-of-sound adjustments may be automatically controlled. In some embodiments, the ultrasound imaging control system may be configured to try out different coarse and/or fine speed of sound values until a desired image quality metric (e.g. sharpness of edges or points, maximum contrast, maximum dynamic range, etc.) of the resulting image (or images) exceeds a threshold value. Alternatively any other "autofocus" algorithms may be applied to adjust a speed-of-sound value until an image quality metric is improved or optimized.

In some cases, each unique pair of transmit aperture and receive aperture may be referred to herein as a "view." In other cases, a view may also refer to a unique combination of a single transmit transducer element and a single receive transducer element. In embodiments in which receive apertures comprise a plurality of transducer elements, the groups of receive elements may be treated collectively for the purposes of the following descriptions. Alternatively, even when part of a receive aperture group, individual receive elements may be treated individually in some embodiments. For example, if a multiple aperture imaging system utilizes 30 transmit apertures and three receive apertures, each image pixel is potentially formed by the combination of image data from 90 different views. Alternately, treating each view as a combination of an individual transmit element and an individual receive element, and considering a probe with 48 transmit elements and 144 receive elements, each pixel may potentially be formed by the combination of image data from 6,912 distinct views. Images obtained from such views may be aggregated through image layer combinations (e.g., as described above) to produce a smaller number of images or image frames.

Unless otherwise specified, the grid 20 of FIGS. 2, 3, 6, 7 and 9 simultaneously represents a grid of display pixels and a grid of corresponding points within a region of interest ("ROI") in an object being imaged. The term "ROI points" will be used herein to describe points within the scan plane (or 3D scan volume) at fixed locations relative to the probe. As will become clear from the following description, ROI points will not necessarily always correlate directly to pixel locations. For example, if an image is "zoomed in" to represent a smaller area 30, the grid of display pixels 20 would correspond only to the points within the zoomed area 30 in the region of interest. However, at any zoom level, the physical location of an ROI point represented by a given image pixel may be determined (relative to the probe) with a high degree of accuracy.

In some embodiments, a speed-of-sound value used during beamforming may be based on a calculation of an average speed-of-sound through a number of different materials, each material having a known average speed-of-sound. For example, when imaging a human patient, ultrasound waves may pass through and reflect from multiple different tissue types. Each type of tissue typically has a slightly different fundamental speed-of-sound. By identifying approximate dimensions of all of the tissues through which a given sound wave passes between a transmit transducer element and a reflector and between the reflector and a receive transducer element, an average speed-of-sound may be calculated for the complete sound wave path. In some embodiments, a weighted average may be used in which each material-specific speed-of-sound value is weighted by a weighting factor that is proportional to a thickness of the material in the image plane. In some embodiments, performing such a calculation may provide a more accurate average speed-of-sound value for use during a beamforming process which may improve the quality beamforming results relative to results obtained using a generic average speed-of-sound value.

In some embodiments, computer-automated-detection techniques (e.g., various heuristic models) may be used to automatically identify one or more tissue types within a patient, based on information such as a shape, position, reflectiveness, or other characteristics of the tissue(s). Alternatively, a user may identify tissues based on his or her own expertise and through the use of a suitable user interface (e.g., by circumscribing an organ in an ultrasound image obtained by beamforming using an assumed speed-of-sound value).

In other embodiments, such techniques may be used in non-medical imaging contexts, such as industrial non-destructive testing. In such embodiments, the dimensions, structures and materials of an object to be imaged may be substantially known. Thus, average speed-of-sound values may be calculated based on a known structure of the object and a known position of the transducer relative to the object.

Introducing Weighting Factors

In any of the various embodiments described herein, weighting factors may be applied at any appropriate point during the process of image formation, from the receiving of analog echo signals through image layer combining to produce final image frames. For example, in some embodiments, some weighting may be applied to signals received from one or more transducer elements when analog echo signals are received by an AFE (212 in FIG. 1B), during analog-to-digital conversion of echo signals by an A/D converter (214 in FIG. 1B), during beamforming performed by a beamforming module (232 in FIG. 1B), or during image layer combining as performed by an image layer combining module (234 in FIG. 1B).

In some embodiments, weighting factors may be applied during beamforming by multiplying individual pixel values by a corresponding weighting factor as each pixel is formed from received echoes. Alternatively, a single weighting factor may be applied to all pixels in an entire image during beamforming, such as when a weighting factor is to be applied to all pixels involving an identified transmit or receive transducer element. Applying weighting factors during beamforming means that a most basic image layer may be improved using weighting factors. In some cases, applying weighting factors during beamforming may be more computationally intensive than applying them later in an image layer combining process, but such low-level image layers may also retain more original information. In some embodiments, computational intensity may need to be balanced against image quality in order to maximize a result using a particular system.

Prior to combining image layers at any of the three levels described above, any individual image layer may be adjusted by applying one or more weighting masks to increase or decrease the contribution of the entire image layer or only a portion of the image layer to a final combined image. In some embodiments, after applying a weighting mask and/or after combining image layers, a normalizing step may be applied in order to cause all regions of a final image (e.g., a third-level image) to have a consistent average intensity.

For any given ROI point and corresponding pixel, some views will provide higher quality image data while other views may contribute lower quality data to the pixel. In some embodiments, one or more weighting factors may be used to increase the effect of high quality views on a displayed pixel and/or to diminish the effect of low quality views on a displayed pixel. For example, during image processing, the intensity magnitude of any given pixel $I_p$ may be obtained by multiplying the pixel intensity values from each contributing image layer by one or more corresponding weighting factors, and then summing the products. For example: $I_p = \Sigma w * I_v$. Where w is a weighting factor and is the intensity obtained by a particular view (v). Such individual weighting factors may be combined into a mask to be applied to an entire image layer.

In some embodiments, weighting factors may be pre-calculated for a for a given set of pixel-view combinations, ROI point-view combinations, combinations of transmit aperture and a pixel or ROI point, or combinations of receive aperture (or receive element) and a pixel or ROI point. Such pre-calculated weighting factors may be stored for later retrieval, such as by a table lookup operation during imaging. In other embodiments, weighting factors may be calculated or otherwise determined "on-the-fly" during imaging. In some embodiments, a different weighting factor may be obtained for each unique pixel-view pair (and/or ROI point-view pair). In some embodiments, the quality of imaging data provided by a view with respect to a given pixel/ROI point may be evaluated in terms of a plurality of factors, two examples of which include signal-to-noise (S/N) ratio and point spread function (PSF).

Weighting Factors Based on S/N Ratio

As used herein, the S/N ratio is a function of attenuation of an ultrasound signal as it passes through an imaged medium. Thus, in some embodiments, signal-to-noise ratio S/N may be predicted as a function of path length. Path length refers to a total distance from a transmit aperture, to an ROI point and back to a receive aperture. In general, an ultrasound signal will attenuate at a somewhat constant rate for each unit of length traveled through a medium. Attenuation rates are well understood by those skilled in the art, and may be a function of an imaging medium, ultrasound frequency, the angle between the signal path and the surfaces of both the transmit and receive elements, and other factors.

Figure 4:
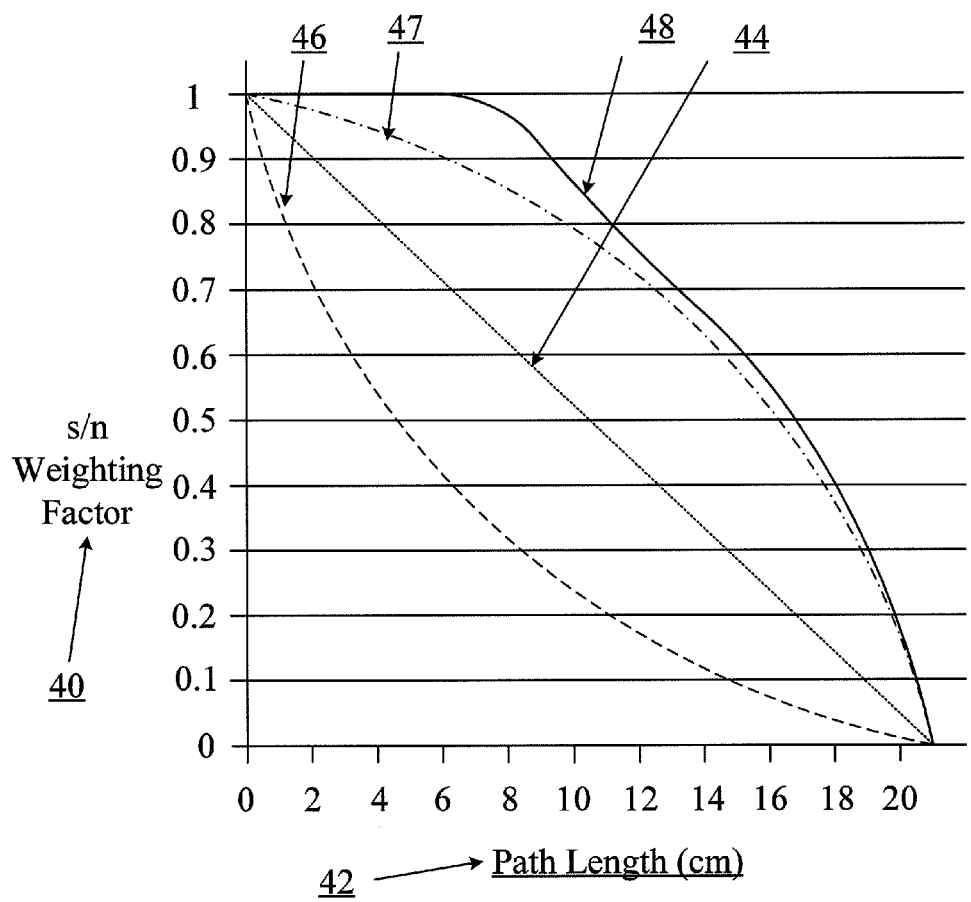
FIG. 4 is a graph illustrating several embodiments of transfer functions that may be used to determine weighting factors based on a total path length from a transmit aperture to a reflector back to a receive aperture.

Therefore, all else being equal, echoes from objects close to an element will tend to be stronger and have better signal-to-noise ratios than echoes from objects that are far away from an element. Thus, in some embodiments, a total distance between transmit and/or receive apertures and an ROI point corresponding to a display pixel may be determined and a table of weighting factors may also be calculated as a function of such total distance. For example, FIG. 4 illustrates examples of relationships between S/N weighting factors 40 (vertical axis) that may be applied to displayed pixels and total path length 42 (horizontal axis). For example, in some embodiments the S/N weighting factor 40 may vary linearly 44 as a function of path length. In other embodiments, the S/N weighting factor 40 may vary as a function of path length 42 exponentially 46, geometrically or according to any other transfer function curve such as parabolic functions, normal distributions, lognormal distributions, Gaussian distributions, Kaiser-Bessel distributions, etc. In some embodiments, relationships between total path distance and a desired S/N weighting factor may be pre-computed using one or more transfer functions and stored in a lookup table such that, during imaging, an imaging system may look up a weighting factor based on a determined path length without performing substantial calculations.

In some embodiments, a path length may be pre-calculated for each combination of view and ROI point. Such path lengths and/or desired weighting factors may then be stored in a lookup table which may be accessed in order to obtain weighting factors during imaging. In other embodiments, a path length may be estimated or calculated based on a time delay between transmitting a ping and receiving an echo using an assumed speed of sound in the medium being imaged. Thus, in some embodiments, a weighting factor may be dynamically determined based on time delays determined during beam forming.

Weighting Factors Based on Point Spread

In other embodiments, weighting factors may be used to improve the overall point spread function (or impulse response) of an imaging system. The point spread function (PSF) is well known to those skilled in the art of ultrasound imaging. PSF is the generalized "impulse response" of any imaging system, whether acoustic, optical, or other electro-magnetic radiation. In other words, a figure of merit for any imaging system is the degree to which a "point" (impulse) in the examination field is smeared in the component (image layers) and/or final images. For the purposes of the present description, point spread refers to the degree to which an imaging system 'smears' or spreads a representation of an object that should appear as a point. The point spread function for any given ROI point (or represented pixel) may be determined as a function of the transmit angle and/or receive angle relative to a given ROI point. Other factors affecting point spread may include the depth of the ROI point, the degree of coherence, the total aperture width, individual aperture widths, ultrasound frequency, and other factors.

Figure 5:
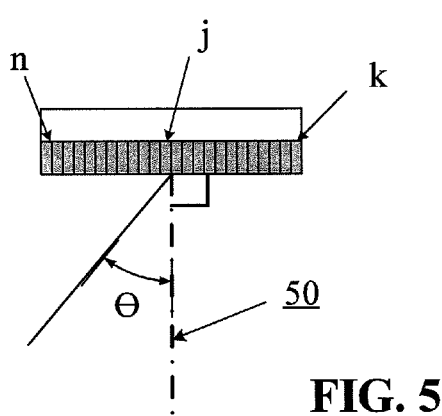
FIG. 5 is a cross-sectional view of an ultrasound transducer array illustrating an effective angle of the transducer elements.

Ultrasound transducer elements are generally most effective at transmitting and receiving ultrasound signals in a direction perpendicular to the element's surface (i.e., along line 50 in FIG. 5). The sensitivity of a transducer element tends to decrease as the angle θ of transmission or reception increases. At some angle θ, image data obtained from an element may have too little signal strength to be useful and/or too much noise or point spread to provide valuable image data. This is true for both transmit angles and receive angles. (Transmit angles and receive angles may be referred to herein generically as "look angles"). As a result, in some embodiments, it may be determined that, for a given pixel, data from a particular transmit aperture, a particular receive aperture or a particular view (i.e., a particular combination of transmit aperture and receive aperture) may be useful in forming an image of the pixel, but less so than data from other apertures or views that may contribute to an image of the pixel. In such cases, a fractional weighting factor may be applied to such lower quality image data in order to decrease its overall contribution to an image or to one or more pixels of an image. In other embodiments, integer weighting factors may also be used.

In some cases, an ideal range of transmit and/or receive angle may depend on factors such as the material of a transducer array, the size or shape of transducer elements, manufacturing methods, element cut shapes, the age of an array, the ultrasound frequency to be transmitted, the voltage or power applied during ultrasound signal transmission, or other factors. In some cases, weighting factors may be applied based on whether a transmit angle or a receive angle exceeds a particular threshold value. For example, in some embodiments when ultrasound signals are transmitted or received at angles θ greater than a certain threshold, the signal power may drop dramatically to such a point that the signal is overwhelmed by random noise even for relatively small total distances traveled from a transmitter to an ROI point and back to a receiver. In such cases, even though the s/n ratio due to path-length attenuation may be very high, the s/n ratio due to the contributions of transducers at transmit or receive angles in excess of a threshold may be very low. In some embodiments, the value of such a threshold angle may be determined by experimentation for a particular transducer type. In other embodiments, the value of a threshold angle may be selected based in part on one or more operating parameters such as a transmit frequency, a transmit power, a transmitted pulse shape, or other factors. In some embodiments, some transducers may have a threshold angle of about 60°, 75°, or 80°. Other transducers may have larger or smaller quality threshold angles.

In some embodiments, weighting factors may be applied in a binary fashion based on whether a transmit angle or a receive angle for a given ROI point exceeds a threshold value. For example, in some embodiments, a weighting factor of "1" may be used for all combinations of ROI point and transducer element for which the angle θ (TX or RX) is less than or equal to a threshold angle, and a weighting factor of "0" may be used for any combinations for which the angle θ exceeds the threshold. In other embodiments, such effects may be counteracted using weighting factors that are proportional to an angle θ. In other embodiments, a combination of such approaches may be used, such as by using a transfer function as described in more detail below.

Figure 6:
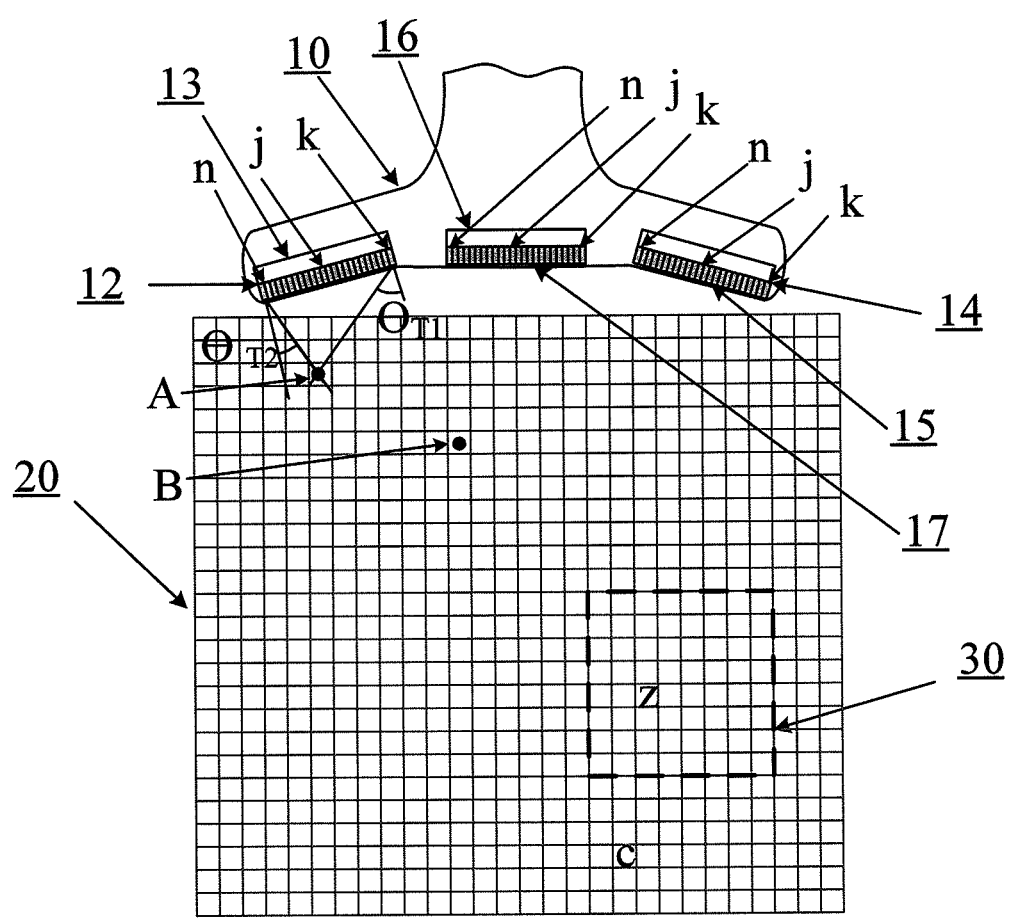
FIG. 6 is a schematic illustration of the probe of FIG. 2 showing two example transmit angles for a selected point and selected transmit apertures.

FIG. 6, illustrates two transmit angles relative to pixel 'A.' In the illustrated example, a first transmit angle $\theta_{T1}$ is shown between transmit aperture Lj and point 'A'. A second transmit angle $\theta_{T2}$ is shown between transmit aperture Lj and point 'A'. As shown, the first transmit angle $\theta_{T1}$ is substantially larger than the second transmit angle $\theta_{T2}$. As a result of this difference in transmit angle, an image of point 'A' formed by pings from transmit aperture Ln will be of higher quality than an image of point 'A' formed by pings from transmit aperture Lj since transmit angle $\theta_{T2}$ is smaller than transmit angle $\theta_{T1}$. Thus in some embodiments using this example, image layers formed by pings from transmit aperture Ln may have a larger weighting factor for point 'A' than image layers formed by pings from aperture Lj. In some embodiments, the actual and relative values of such weighting factors may be determined as a function of the relevant transmit angles based on a transfer function (examples of which are described below). In some embodiments, a transmit angle may be measured relative to the center of a transmit aperture.

Figure 7:
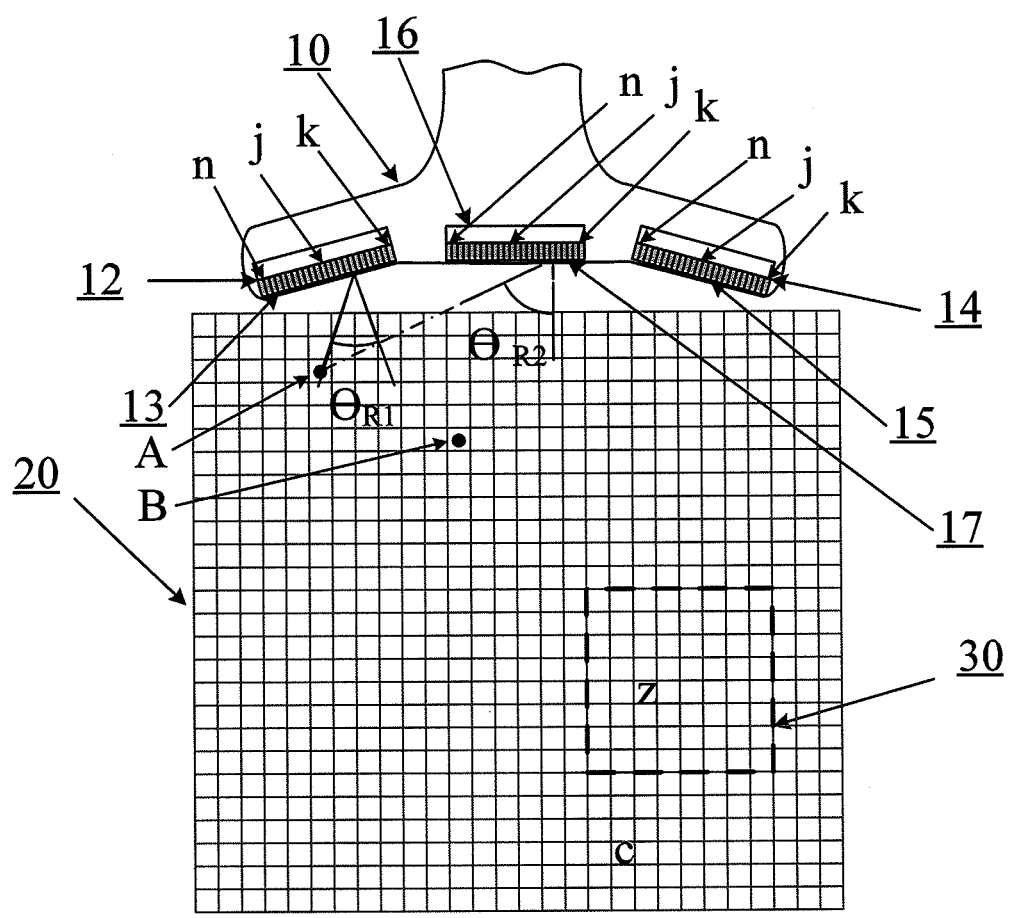
FIG. 7 is a schematic illustration of the probe of FIG. 2 showing two example receive angles for a selected point and selected receive apertures.

In a similar manner, some embodiments of a multiple aperture imaging system may apply weighting factors based on receive angles. FIG. 7 illustrates two different receive angles receiving echoes of a reflector at point 'A'. A first receive angle $\theta_{R1}$ is shown between an element of the left transducer array 12 and point 'A,' and a second receive angle $\theta_{R2}$ is shown between point 'A' and an element on the center transducer array 17. As shown, the first receive angle $\theta_{R1}$ is substantially smaller than the second receive angle $\theta_{R1}$. As a result of this difference in receive angle, an image of point 'A' formed by echoes received at the left receive aperture 13 will be of higher quality than an image of point 'A' formed by echoes received at the center receive aperture 17 since receive angle $\theta_{R1}$ is smaller than receive angle $\theta_{R2}$.

In the illustrated embodiments, each receive aperture has a substantial width comprising a plurality of receive elements. Thus for example, a receive angle between point 'A' and a receive element at the far left edge of the center receive aperture 17 will be smaller than a receive angle between point 'A' and a receive element at the far right edge of the same center receive aperture 17. Thus, in some embodiments, when determining a weighting factor based on a receive angle, the receive angle may be defined as an angle between the given ROI point and a center of the receive aperture. In other embodiments, a receive angle may be defined as a maximum receive angle experienced by a group of transducer elements in an aperture. Similarly, any of these methods may also be used for selecting a transmit angle for transmit apertures comprising more than one transmitting transducer element.

In other embodiments, weighting factors may be used to correct for combinations of transmit and receive apertures (i.e., "views"). The effect of poorly-contributing views may be mitigated in several ways. In some cases, a poorly-contributing view may be completely eliminated by ignoring echo data received from a particular view, such as by using a weighting factor of zero. For example in some embodiments, for a view defined by the transmit aperture Ck and the right receive aperture 15 (e.g., as shown in FIG. 3) may be ignored simply by not using echo data received by the right receive aperture 15 from a ping transmitted by the Ck transmit aperture. Alternatively, if it is determined that all views involving transmit aperture Ck should be ignored, the system may simply skip transmit aperture Ck while cycling through transmit apertures. Alternatively, all echo data received from pings transmitted by aperture Ck may receive a weighting factor of zero (or nearly zero).

In some embodiments, transmit and/or receive angles may be determined in advance for each ROI point and such lookup angles may be stored in a memory device. When a zoom level is selected, the imaging system may identify ROI points corresponding to image pixels and then identify corresponding transmit or receive angles. Once transmit or receive angles are known for a given ROI point in a particular first-level image layer, a weighting factor may be determined as a function of one or both of the transmit and receive angles in order to increase or decrease the effect of the given view on a final pixel value.

Figure 8:
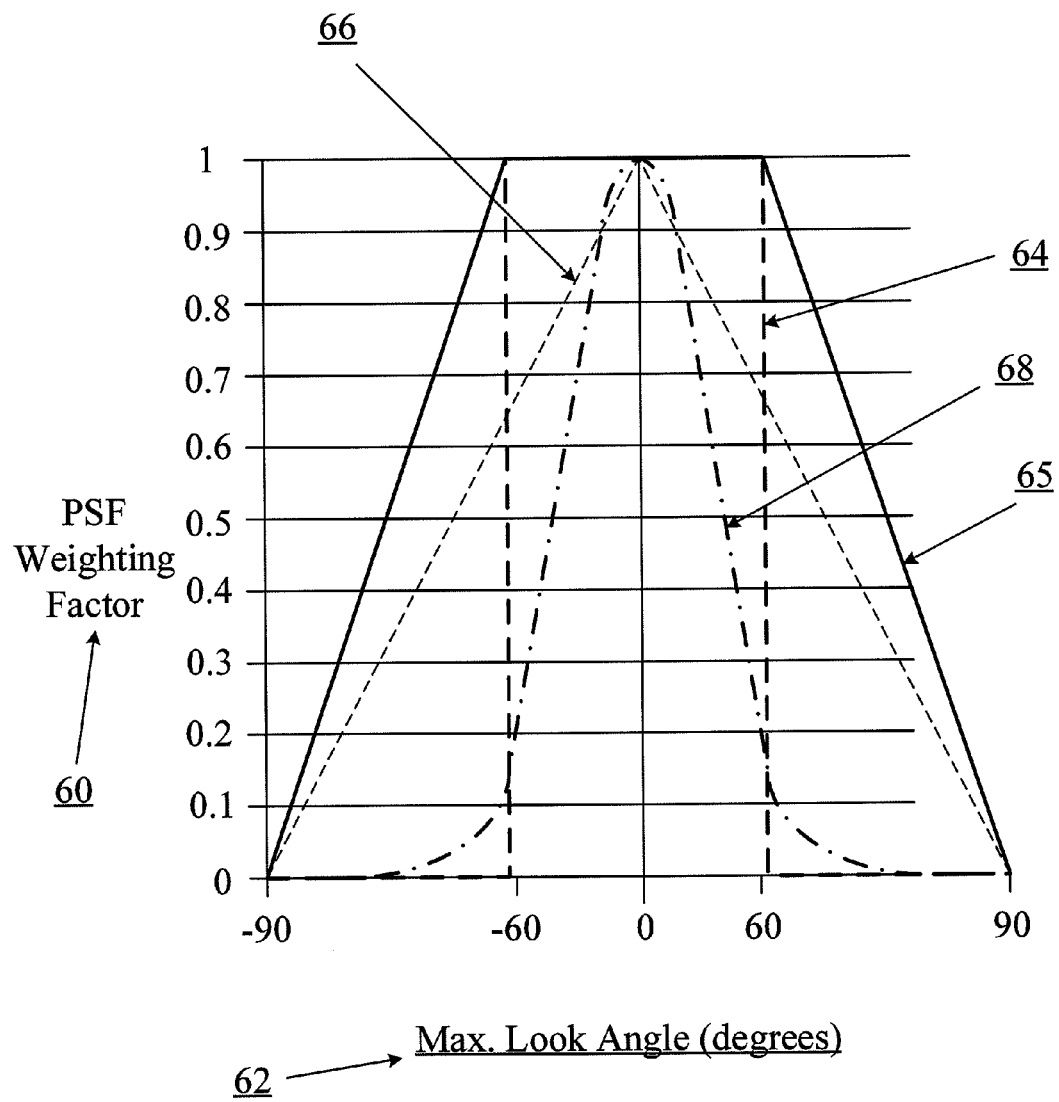
FIG. 8 is a graph illustrating several embodiments of transfer functions that may be used to determine weighting factors based on an aperture transmit angle and/or an aperture receive angle.

FIG. 8 illustrates examples of transfer functions that may be used for determining weighting factors 60 (vertical axis) based on a particular look angle 62 (i.e. either a transmit angle, a receive angle, or a maximum of the two) for any given combination of view and ROI point. A relationship between a look angle 62 and a weighting factor 60 may follow any of a wide range of patterns. In some embodiments, one or more stepwise functions (e.g., functions with a step increase or decrease in weight at a threshold angle) may be used. For example as shown in curve 64 of FIG. 8, weighting factors may be a monotonic function of look angle in which any pixel-view pair with at least one look angle greater than a threshold angle (e.g, about 60°, or $\pi/3$ radians, in the illustrated example) may be given a weighting value of zero, while all pixel-view pairs with both look angles less than the threshold angle may have a weight of one. In other embodiments, weighting factors 60 may be a linear function 66 of look angle, varying from zero to one as an absolute look angle 62 increases. In other embodiments, as shown in Curve 65, a transfer function may assign weighting factors of one for all look angles less than or equal to the threshold angle (e.g., 60° in the illustrated example), and weighting factors may vary linearly from one to zero for look angles greater than the threshold angle. In further embodiments, weighting factors may vary exponentially, geometrically or according to any other transfer function curve, including but not limited to parabolic functions, normal distributions (e.g., as shown by curve 68), lognormal distributions, Gaussian distributions, Kaiser-Bessel distributions, etc. In some embodiments, an ultrasound imaging control system may be configured to include a plurality of selectable look-angle-to-weighting-factor transfer functions that may be selected manually by a user or automatically by an imaging system.

In some embodiments, such transfer functions may be implemented with lookup tables. For example, a lookup table may be constructed using a chosen transfer function and weighting factors may be calculated for several possible discrete values of the relevant input variable (e.g., TX angle, RX angle, path length, or time delay). Then during imaging, an imaging control system may simply determine the input variable quantity and look up a weighting factor value based on the nearest (or interpolated) result value in the lookup table.

In some other embodiments, instead of determining a weighting factor from a transmit and/or receive angle, the point spread for any given ROI point corresponding to an image pixel by each view may be predicted by modeling, or determined empirically using a phantom. In some embodiments, each view may be tested for a given pixel to determine whether each view improves image quality or makes it worse. Repeating this process for each view and for each pixel location, a table of weighting factors may be assembled. For example, with reference to FIG. 3, pixel 'A' may be tested by transmitting a first ping from transmit aperture Ln and receiving echoes on the Center receive aperture 17, then transmitting a second ping from transmit aperture Lj and receiving echoes on the Center receive aperture 17. The results of the two views may then be compared to determine which view provides higher quality data for forming pixel A. In some embodiments, such a testing method may be carried out automatically by modeling the conditions of a given imaging system and a given multiple aperture probe.

In some embodiments, a lookup table may be assembled to represent the results of testing each view for each pixel. For example, a lookup table may include a weighting value for each unique combination of pixel and view (referred to herein as a pixel-view pair). In some embodiments, such weighting values may be binary such that data from each view either contributes to a pixel or is ignored. In other embodiments, weighting values may be fractional values, such that each view contributes to a pixel in proportion to a weighting factor (e.g., 0% to 100% of data acquired for each view may contribute to a given pixel's displayed value). In some embodiments, such fractional weighting factors may be determined by using a transfer function based on any suitable variable related to a degree of expected point spread.

One challenge with maintaining a lookup table of weighting values for each pixel-view pair is that pixel-view relationships change as an image is "zoomed" or "panned" to display different portions of the insonified regions. For example, if the pixel grid 20 is assumed to be a complete insonified region, and a user "zooms in" on a particular region 30 of the insonified region, the information within the zoomed region 30 will be enlarged to occupy the entire display pixel grid 20. In that case, the ROI points corresponding to displayed pixels will be substantially different relative to the transmit and receive apertures of the probe as compared with a fully zoomed-out image. As a result, the contribution of each view to each new pixel may be substantially different than in the original "un-zoomed" image. For example, if a selected zoomed region is small enough and sufficiently far from the probe, every value of a weighting mask may simply be one.

In some embodiments, this challenge may be addressed by computing and storing pixel-view weighting values for a plurality of discrete zoom levels or pan locations. In such embodiments, separate weighting value tables would be needed for each pre-computed zoom level. In some embodiments, weighting values for zoom levels in between pre-computed zoom levels may be interpolated, or the nearest table may be used. In other embodiments, weighting factors may be determined on-the-fly using a transfer function to identify a weighting factor based on a measurable or detectable variable quantity such as transmit angle or receive angle as described above.

Combining Weighting Factors

In some embodiments, SN weighting factors may be combined with point spread weighting factors, look angle threshold weighting factors, transmit frequency weighting factors and/or weighting factors of any other type. In some embodiments, multiple distinct weighting factors may be combined by simple arithmetic averaging. In other embodiments, weighted arithmetic averaging may be used to increase or decrease the relative impact of one type of weighting factor relative to one or more other type. As discussed above, the intensity magnitude of any given pixel $I_p$ may be obtained by: $I_p = \Sigma w \ast I_v$. Where w is a weighting factor and $I_v$ is the intensity obtained by a particular view (v). Thus, in some embodiments, the weighting factor 'w' may be determined by: $w = Aw_1 + Bw_2$, where A and B are weighted average coefficients, and $w_1$ and $w_2$ are different types of weighting factors. For example, if the coefficients A & B are both 0.5, then equal weight will be given to the weighting factors $w_1$ & $w_2$. On the other hand, for example, if A is 0.75 and B is 0.25, $w_1$ will be given three times the weight of $w_2$. In further embodiments, weighting factors of multiple types may be combined by more complex normalizing algorithms which may be based on factors such as the type of weighting factor, the location of pixels, or other factors. Any other combining or normalizing algorithms may also be used. Any of the above approaches to combining weighting factors may be applied to pixel-specific tables of weighting factors, array-specific tables, or scalar weighting factors.

In other embodiments, a common weighting factor may be applied to all or any portion of one or more first-level image layers. For example, if it is determined that a given transmit aperture is providing low quality imaging data, all pixels may have a weighting factor of zero for all views or image layers containing data obtained from that transmit aperture.

In some embodiments, an ultrasound imaging system may include manual or automatic controls configured to allow for manual or automatic adjustment of weighting factors by aperture. For example, in some embodiments, an ultrasound imaging system may include an array of sliders (or other physical or virtual control devices), with one slider for each transmit aperture. Adjusting such sliders may increase or decrease a weighting factor for a particular transmit aperture for all views. Similarly, such controls may be provided for each receive aperture. For example, while imaging a region of interest, a user may adjust a given aperture control in order to increase or decrease a contribution of that aperture to the displayed image until the user determines that an adequate or optimal image has been obtained.

In further embodiments, a multiple aperture imaging system may be configured to automatically increase or decrease weighting factors for individual transmit and/or receive apertures or elements until a desired image quality metric is optimized. In some embodiments, image quality metrics that may be optimized by adjusting weighting factors may include image sharpness, contrast, dynamic range, point spread, or other metrics. In some embodiments, optimization may comprise identifying a group of weighting factors that maximizes the selected image quality variable. In other embodiments, optimization may comprise identifying a group of weighting factors that minimizes the selected image quality variable. In still other embodiments, optimization may comprise maximizing or minimizing a group of image quality variables while remaining within additional constraints. In various embodiments, when applying weighting factors to a collection of transducer elements (or apertures), a single scalar may be stored and applied to all relevant pixels rather than storing and applying a table of weighting factors.

Transmitting Multiple Ping Frequencies

In other embodiments, weighting factors may be developed to normalize the effect of other factors that may otherwise cause some transmit or receive elements to have a distorting effect on a final image. For example, in some cases an ultrasound probe may include one or more transmit transducer elements configured to transmit ultrasound signals with different power levels, different fundamental frequencies, different pulse shapes and/or different pulse lengths as compared with other transmit (and/or receive) transducer elements. In such cases, it may be desirable to increase or decrease the relative contribution of echoes from such transducer elements to a final combined image. As with the previous embodiments, such transmit and/or receive elements may be weighted individually or in groups according to manual controls or automatic algorithms. Such additional weighting factors may also be combined with other types of weighting factors as described above.

For example, as is generally understood by those skilled in the art, high frequency pulses can produce higher quality images but cannot penetrate as far into the body. On the other hand, lower frequency pulses may penetrate deeply, and may therefore produce higher quality images of deeper tissue, but will tend to produce lower quality images of shallow tissue compared with higher frequency pulses. Thus, in some embodiments, an ultrasound imaging system may be configured to transmit and receive low-frequency pulses to image deep regions of an image frame. The same system may also be configured to transmit and receive high frequency pulses to image relatively shallow regions of the image frame. In such a system, low-frequency image layers may be combined with the high-frequency image layers to improve the quality of all regions of a combined image. In some embodiments, weighting factors may be used to increase the contribution of deep regions of the low frequency image layer, to increase the contribution of shallow regions of the high frequency image layer, and to smooth a transition between the deep and shallow regions.

In similar ways, further embodiments may be configured to adjust a transmit signal (e.g. by adjusting a transmit pulse frequency, shape, time length, etc.) to optimize one or more selected regions of an image frame, and the resulting regionally-optimized image layer may be combined with other image layers that may be optimized in different regions. In other examples, regionally-optimized image layers may be combined with image layers that are not regionally optimized. In some embodiments, weighting factors may be used to smooth transitions or to otherwise improve the quality of a combined image. For example, weighting factors may be used to increase the contribution of pixels within an optimized region of an image while decreasing the contribution of non-optimized image regions. In further embodiments, weighting factors may be used to smooth a transition between an optimized region of one image layer and adjacent regions of other image layers.

In some embodiments, after applying any weighting masks and/or after combining image layers, a normalizing step may be applied in order to cause all regions of a final image (e.g., a third-level image) to have a consistent average intensity. For example, without normalizing pixel intensities, lateral and/or corner regions of a final image may be substantially less bright than a central region of the image due to the application of weighting factors. Thus, in order to provide a more consistent image, intensity levels for all pixels in an entire image may be normalized to fall within a desired range. In some embodiments, such normalization may be achieved by techniques similar to those employed by a lateral gain control of a standard ultrasound imaging system, which increases brightness of otherwise relatively "dim" pixels at lateral edges of an image.

Weighting Factors to Avoid Obstacles

Figure 9:
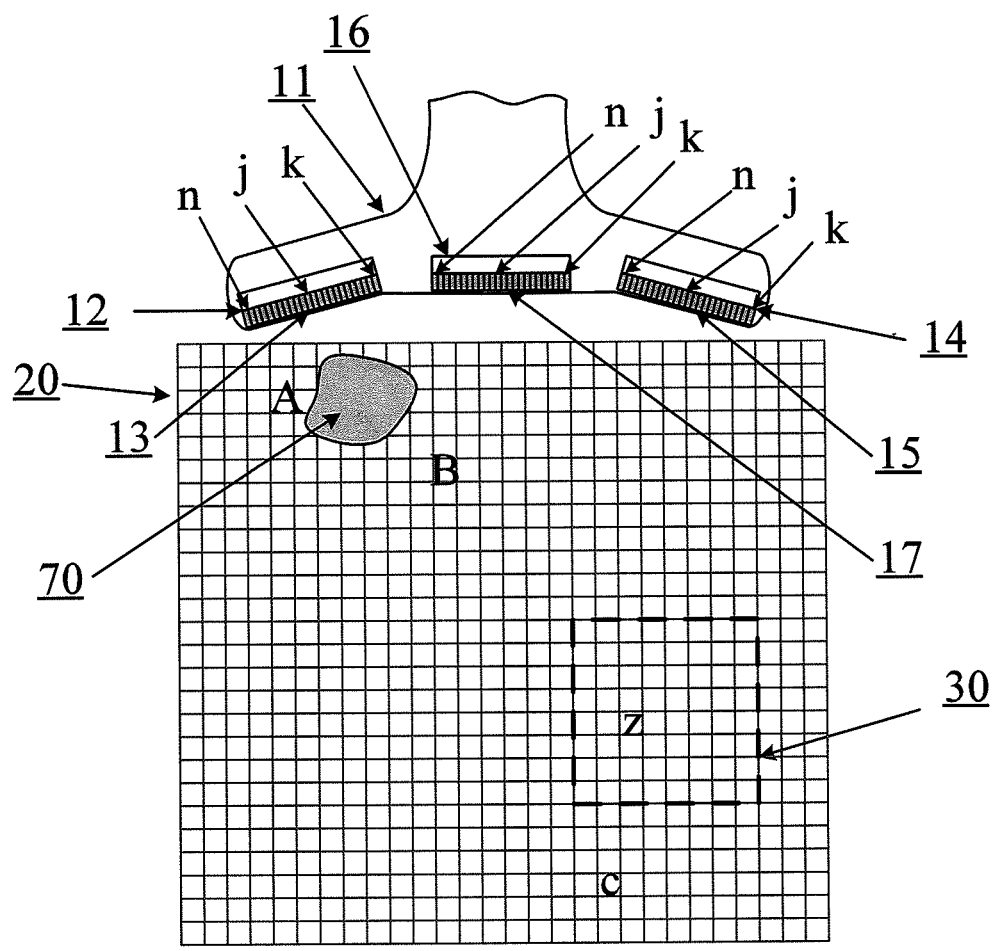
FIG. 9 is a schematic illustration of a multiple aperture ultrasound imaging probe with three transducer arrays and a grid of points/pixels to be imaged, with an obstacle between the probe and the image field.

FIG. 9 illustrates an ultrasound imaging scenario in which some transmit transducers of a multiple aperture probe 11 are partially or completely obscured by an obstacle 70. In some embodiments, the obstacle 70 may be a rib or other bone in a human or animal subject. In other embodiments, an obstacle may be a material with a very high or very low inherent speed-of-sound relative to surrounding material being imaged. For example, bone has a high inherent speed of sound relative to tissue, and an air-filled organ such as a lung will typically have a much lower speed-of-sound than surrounding tissues. Alternatively, any other structure that interferes with a desired image may be interpreted as an obstacle. Multiple aperture ultrasound imaging systems may produce an image using an un-modified multiple aperture imaging technique in the scenario of FIG. 9, but the obstacle will typically cause a bright "halo" effect in the near field and a shadow beyond the obstacle, since a hard obstacle will echo substantially all of the ultrasound energy transmitted toward it. By contrast, with single-aperture (and especially phased-array) imaging systems, any obstacle will tend to entirely eclipse a substantial section of image data beyond the obstacle, resulting in a null set of image data for the eclipsed region. Thus, in some embodiments, it may be desirable to ignore or reduce the effect of transmit pings from transmit apertures that are entirely or partially obscured by an obstacle. In some embodiments, a degree of obstacle blockage may be determined and then a weighting factor may be selected as a function of the degree of blockage.

As an example, when trying to image tissue behind obstructions such as ribs, an imaging system using ping technology can be configured to make use of signals returning from the deep tissues and can, to a large extent, ignore the signals that were blocked. However, when the beamformer does incorporate the signals that are received after a blocked transmission, channel noise is typically added into the image. For this reason, it is desirable to detect blocked transmitters and not use the corresponding received signals which are mostly noise.

In some embodiments, a trial and error process may be used to identify transmit apertures that are not obscured by obstacles. In some embodiments, a given transmit aperture may be tested by transmitting a ping from that transmit aperture and listening for return echoes at one or more receive apertures. Received echoes with magnitudes greater than some specific threshold value, occurring after relatively long time delays, may indicate that the ultrasound signals are penetrating to a substantial depth within the region of interest, and the test transmit aperture therefore may be qualified as being essentially free of blocking obstacles. In some embodiments, transmit apertures that return no deep echoes at all may be interpreted as being entirely blocked by an obstacle. However, this is an imperfect method because a lack of deep echoes may also indicate very anatomically and acoustically uniform material or some other material that simply doesn't contain any significant reflectors at the test depth.

In other embodiments, it may be preferable to directly identify blocked transmit apertures rather than attempting to identify unblocked transmit apertures. In some embodiments, a transmit aperture may be tested for blockage by transmitting a ping and evaluating return echoes in the near field using, for example, a temporal gating or windowing mechanism to eliminate potential false positive results due to anticipated strong echoes occurring at or just above the skin surface. This may be important to preclude strong echoes likely to be received from the transducer-to-lens interface, the lens-to-gel interface, and the gel-to-skin interface from being incorrectly interpreted as blocking obstacles. Accordingly, the test depth can be restricted by establishing a temporal "starting point" for return echoes to be examined, and samples arriving prior to the start of the window are likely interface echoes that can safely be ignored. Similarly, a temporal "ending point" for strong return echoes can be established to rule out deep structures beneath the region of interest from being classified as blocking obstacles; any such echoes detected may also be ignored. If the echoes received from a test ping are substantially strong ones with time delays occurring within the appropriately defined gate or window, a hard blocking obstacle is likely present between the probe and the region of interest, and the test transmit aperture may be classified as being potentially blocked by this obstacle. If a test ping does not return any substantially strong echoes within the appropriately defined test depth, that transmit aperture may be assumed to be clear of blocking obstacles. In some embodiments, the degree or extent of blockage may be evaluated by analyzing the patterns of strong shallow echoes and deeper echoes occurring at multiple receive apertures.

In some embodiments, a test depth at which an obstacle is anticipated can differ based on variability of the body or object under inspection. For example, substantial variation in the thickness of a fat layer over the ribs from one patient to another may cause significant variation in the test depth at which the imaging system may evaluate echoes to identify obstacles. In some embodiments, a variable window/depth control may be provided to allow manual or automatic adjustment of an evaluation depth for identifying obstacles. For example in some embodiments, a test-depth control may be set to evaluate echoes at depths between 1 mm and 1 cm (or more) below the probe. Such a control may be adjusted to evaluate echoes at various depths in order to locate a range of depths returning strong echoes indicating the presence of an obstacle. In some embodiments, the width of such a test window may be held constant while seeking echoes at various depths. In some embodiments, a range of depth at which the system may search for obstacles may be determined automatically. In such embodiments, a probe may be placed over a known (or expected) obstacle, and a process may be initiated in which an imaging control system transmits pings and "listens" for strong echoes within a particular depth range.

In some embodiments, weighting factors may be applied to transmit apertures based on a degree to which each transmit aperture is obscured by an obstacle. For example, a transmit aperture that is entirely obscured by an obstacle may receive a weighting factor of zero (or a value substantially near zero). A transmit aperture that is entirely clear (i.e. not obscured by any obstacles at all) may have a weighting factor of one (or substantially near one). In some embodiments, partially or entirely blocked transmit apertures may have weighting factors applied with respect to all receive apertures. In other embodiments, partially or entirely blocked transmit apertures may have weighting factors applied with respect to only some receive apertures. In still other embodiments, weighting factors may be applied based on ROI point location, such as applying different weights for shallow ROI regions above a blocking obstacle relative to regions below (i.e., blocked by) the obstacle. For example, ROI points above an obstacle may receive weighting factors of about one, while ROI points below the obstacle may receive a weight of about zero.

In some embodiments, transmit apertures that are only partially obscured may have weighting factors between zero and one in proportion to a degree of blockage. With reference to FIG. 9, transmit aperture Lj may be interpreted as entirely blocked by the obstacle 70, since nearly all of the energy transmit by aperture Lj will be reflected by the obstacle 70. However, aperture Lk is only partially blocked by the obstacle 70 and some substantial amount of energy transmitted by aperture Lk will pass through the region of interest and will be reflected to at least the center 17 and right 15 receive apertures. Transmit aperture Ln is partially blocked by the obstacle 70, since some ultrasound energy will still pass through the region of interest around the obstacle 70. In some embodiments, weighting factors may be applied to transmit apertures alone in order to improve image quality in the area of a detected obstacle. For example, in the situation illustrated in FIG. 9, a weighting factor for all image pixels may resemble the following:

TABLE 1

Weighting Factors for a Blocked TX Aperture

|        | RX Left |
|--------|---------|
| TX Ln  | 0.3     |
| TX Lj  | 0       |
| TX Lk  | .5      |
| TX Cn  | 1       |
| TX Cj  | 1       |
| TX Ck  | 1       |
| TX Rn  | 1       |
| TX Rj  | 1       |
| TX Rk  | 1       |

In other embodiments, both individual transmit elements and individual receive elements may be weighted to address detected obstacles. For example, in the situation illustrated in FIG. 9 (and assuming that the elements Ln, Lj, Lk, Cn, Cj, Ck, Rn, Rj, and Rk may also be used as receive elements), a weighting factor table for all image pixels may resemble the following:

TABLE 2

TX and RX Weighting Factors for a Blocked TX Aperture

|       | RX Ln | RX Lj | RX Lk | RX Cn | Rx Cj | RX Ck | RX Rn | RX Rj | RX Rk |
|-------|-------|-------|-------|-------|-------|-------|-------|-------|-------|
| TX Ln | 0.3   | 0.0   | 0.4   | 0.5   | 0.5   | 0.5   | 0.5   | 0.5   | 0.5   |
| TX Lj | 0.0   | 0.0   | 0.0   | 0.0   | 0.0   | 0.0   | 0.0   | 0.0   | 0.0   |
| TX Lk | 0.4   | 0.0   | 0.5   | 0.7   | 0.7   | 0.7   | 0.7   | 0.7   | 0.7   |
| TX Cn | 0.5   | 0.0   | 0.7   | 1     | 1     | 1     | 1     | 1     | 1     |
| TX Cj | 0.5   | 0.0   | 0.7   | 1     | 1     | 1     | 1     | 1     | 1     |
| TX Ck | 0.5   | 0.0   | 0.7   | 1     | 1     | 1     | 1     | 1     | 1     |
| TX Rn | 0.5   | 0.0   | 0.7   | 1     | 1     | 1     | 1     | 1     | 1     |
| TX Rj | 0.5   | 0.0   | 0.7   | 1     | 1     | 1     | 1     | 1     | 1     |
| TX Rk | 0.5   | 0.0   | 0.7   | 1     | 1     | 1     | 1     | 1     | 1     |

In some embodiments, a general smoothing function may be applied based on expected geometry of a particular type of obstacle. For example, if it is known that expected obstacles are ribs, certain assumptions can be made regarding the geometry of detected obstacles, such as a range of anticipated rib size, spacing between ribs, ranges of depth at which ribs may be found, etc. In some embodiments, such information may be used to correct measurement errors. For example, an indication that an ostensibly un-blocked transmit aperture is positioned in between two or more closely spaced blocked apertures could be safely interpreted as an error. As a result, the ostensibly unblocked transmit aperture may be ignored and may be treated as "blocked." Similarly, if the spacing between ribs is assumed to fall within a known range, an indication that a blocked transmit aperture is positioned between two or more closely spaced clear apertures may also be interpreted as an error.

In other embodiments, known or assumed information about the geometry of obstacles within a region of interest may be used to smooth a transition between "blocked" and "un-blocked" transmit apertures. For example, during B-mode imaging, transmit apertures that are positioned at an edge of an obstacle can in some cases experience refraction and/or diffraction of the ultrasound signal. Thus, in some embodiments, transmit apertures adjacent to an edge of a detected obstacle may be assigned weighting factors that increase from zero (for blocked apertures) to one (for entirely clear apertures) in steps, thereby minimizing the effect of transmit apertures that may still be adjacent to (and/or partially blocked by) the obstacle. In other embodiments, transmit apertures that are only partially blocked, or that are determined to be too close to detected obstacles may be ignored.

In some embodiments, in addition to improving the quality of B-mode ultrasound images, the identification of "clear" transmit apertures may be beneficial for performing Doppler imaging or Elastography with a multiple aperture probe. Some embodiments of Doppler imaging and Elastography utilize a single transmit aperture for obtaining multiple images at extremely high frame rates (e.g., hundreds or thousands of frames per second). In such embodiments, the above methods may be used to identify one or more suitable transmit apertures that are well clear of any detected obstacles. For example, if two adjacent obstacles are identified (such as two adjacent ribs), an imaging control system may select a transmit aperture that is in between the two obstacles. In some embodiments, such a selected transmit aperture may be equidistant from both detected obstacles.

Any of the foregoing embodiments may be used in combination with a multiple aperture imaging probe of any desired construction. Examples of multiple aperture ultrasound imaging probes are provided in Applicants' prior patent applications, including the following US patent applications: U.S. patent application Ser. No. 11/865,501, filed on Oct. 1, 2007 and titled "Method And Apparatus To Produce Ultrasonic Images Using Multiple Apertures," now U.S. Pat. No. 8,007,439; U.S. patent application Ser. No. 12/760,375, filed on Apr. 14, 2010, published as 2010/0262013 and titled "Universal Multiple Aperture Medical Ultrasound Probe"; U.S. patent application Ser. No. 12/760,327, filed on Apr. 14, 2010, published as 2010/0268503 and titled "Multiple Aperture Ultrasound Array Alignment Fixture"; U.S. patent application Ser. No. 13/279,110, filed on Oct. 21, 2011, published as 2012/0057428 and titled "Calibration of Ultrasound Probes"; U.S. patent application Ser. No. 13/272,098, filed on Oct. 12, 2011, published 2012/0095347 and titled "Multiple Aperture Probe Internal Apparatus and Cable Assemblies"; U.S. patent application Ser. No. 13/272,105, filed on Oct. 12, 2011, published as 2012/0095343 and titled "Concave Ultrasound Transducers and 3D Arrays"; U.S. patent application Ser. No. 13/029,907, filed on Feb. 17, 2011, published as 2011/0201933 and titled "Point Source Transmission And Speed-Of-Sound Correction Using Multi-Aperture Ultrasound Imaging". The entire contents of each of these patents and patent applications is incorporated herein by reference.

Embodiments of the systems and methods described above may also be beneficially applied to multiple aperture ultrasound imaging systems utilizing focused phased array transmit pulses rather than point source transmit pulses (pings). Similarly, embodiments of the systems and methods described above may also be beneficially applied to single-aperture imaging systems using multiple sub-apertures for ping transmission. In still further embodiments, the methods described above may also be applied to conventional ultrasound systems using phased array-transmissions from a single-aperture probe.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. An ultrasound imaging system, comprising:
    a first transmit aperture and a second transmit aperture configured to transmit first and second unfocused circular wave front ultrasound signals into a region of interest;
    a first receive aperture configured to receive echoes of the first and second unfocused circular wave front ultrasound signals;
    a controller configured to form a first image layer from received echoes of the first unfocused circular wave front ultrasound signal, and configured to form a second image layer from received echoes of the second unfocused circular wave front ultrasound signal;
    the controller being further configured to determine a value of a weighting factor by:
        determining a first distance from one of the first or second transmit apertures to a point represented by at least one pixel;
        determining a second distance from the point to the first receive aperture;
        summing the first distance and the second distance to obtain a total path length; and
        determining the weighting factor as a mathematical function of the total path length;
    the controller being further configured to apply the weighting factor to the at least one pixel of the first image layer to obtain a modified first image layer, and to combine the modified first image layer with the second image layer to form a combined image; and
    a display device configured to display the combined image.

2. The system of claim 1, wherein the controller is further configured to apply a weighting factor to at least one pixel of the second image layer to obtain a modified second image layer, and to combine the modified first image layer with the modified second image layer to form a second combined image, and wherein the second combined image is displayed on the display device.

3. The system of claim 1, wherein the controller is further configured to, prior to applying the weighting factor, determine said weighting factor or a different value of the weighting factor as a combined weighting factor formed as a combination of the weighting factor and a second weighting factor obtained by determining an angle between a point represented by the at least one pixel and the first transmit aperture, determine whether the angle exceeds a threshold value, select a first value for the second weighting factor if the angle exceeds the threshold value, or select a second value for the second weighting factor if the angle does not exceed the threshold value.

4. The system of claim 1, wherein the controller is further configured to, prior to applying the weighting factor, determine a value of the weighting factor as a combined weighting factor formed as a combination of the weighting factor and a second weighting factor obtained by determining an angle between a point represented by the at least one pixel and the first receive aperture, determine whether the angle exceeds a threshold value, select a first value for the second weighting factor if the angle exceeds the threshold value, or select a second value for the second weighting factor if the angle does not exceed the threshold value.

5. The system of claim 1, wherein the controller is further configured to, prior to applying the weighting factor, determine a first angle between a point represented by the at least one pixel and the first receive aperture, determine a second angle between a point represented by the at least one pixel and the first transmit aperture, and determine the weighting factor as a combined weighting factor formed as a combination of the weighting factor and a second weighting factor that is determined as a mathematical function of the first angle, the second angle, or both the first angle and the second angle, wherein the mathematical function is selected from the group consisting of a monotonic function, a linear function, a normal distribution, a parabolic function, a geometric function, an exponential function, a Gaussian distribution, and a Kaiser-Bessel distribution.

6. The system of claim 1, wherein the controller is further configured to, prior to applying the weighting factor, determine a value of the weighting factor as a combined weighting factor formed as a combination of the weighting factor and a second weighting factor obtained by evaluating a quality of a point-spread-function of the first transmit aperture and the first receive aperture, determine that a pixel image obtained using the first transmit aperture and the first receive aperture will improve image quality, and assign a non-zero positive value to the second weighting factor.

7. An ultrasound imaging system, comprising:
    a first transmit aperture configured to transmit first unfocused circular wave front ultrasound signals at a first frequency into a region of interest, and configured to transmit second unfocused circular wave front ultrasound signals at a second frequency into the region of interest, the first frequency being greater than the second frequency;

a first receive aperture configured to receive echoes of the first and second unfocused circular wave front ultrasound signals;

a controller configured to form a first image layer from received echoes of the first unfocused circular wave front ultrasound signal, and configured to form a second image layer from received echoes of the second unfocused circular wave front ultrasound signal, the controller being further configured to apply a weighting factor to at least one pixel of the first image layer to obtain a modified first image layer, the weighting factor being based on a difference between the first frequency and the second frequency, and the controller being configured to combine the modified first image layer with the second image layer to form a combined image; and a display device configured to display the combined image.

8. The system of claim 7, wherein the controller is further configured to apply said weighting factor or a different weighting factor to at least one pixel of the second image layer to obtain a modified second image layer, and to combine the modified first image layer with the modified second image layer to form a second combined image, and wherein the second combined image is displayed on the display device.

9. The system of claim 7, wherein the controller is further configured to, prior to applying the weighting factor, determine a value of the weighting factor as a combined weighting factor formed as a combination of the weighting factor and a second weighting factor obtained by determining an angle between a point represented by the at least one pixel and the first transmit aperture, determine whether the angle exceeds a threshold value, select a first value for the second weighting factor if the angle exceeds the threshold value, or select a second value for the second weighting factor if the angle does not exceed the threshold value.

10. The system of claim 7, wherein the controller is further configured to, prior to applying the weighting factor, determine a value of the weighting factor as a combined weighting factor formed as a combination of the weighting factor and a second weighting factor obtained by determining an angle between a point represented by the at least one pixel and the first receive aperture, determine whether the angle exceeds a threshold value, select a first value for the second weighting factor if the angle exceeds the threshold value, or select a second value for the second weighting factor if the angle does not exceed the threshold value.

11. The system of claim 7, wherein the controller is further configured to, prior to applying the weighting factor, determine a first angle between a point represented by the at least one pixel and the first receive aperture, determine a second angle between a point represented by the at least one pixel and the first transmit aperture, and determine the weighting factor as a combined weighting factor formed as a combination of the weighting factor and a second weighting factor that is determined as a mathematical function of the first angle, the second angle, or both the first angle and the second angle, wherein the mathematical function is selected from the group consisting of a monotonic function, a linear function, a normal distribution, a parabolic function, a geometric function, an exponential function, a Gaussian distribution, and a Kaiser-Bessel distribution.

12. The system of claim 7, wherein the controller is further configured to, prior to applying the weighting factor, determine a value of the weighting factor as a combined weighting factor formed as a combination of the weighting factor and a second weighting factor obtained by evaluating a quality of a point-spread-function of the first transmit aperture and the first receive aperture, determine that a pixel image obtained using the first transmit aperture and the first receive aperture will improve image quality, and assign a non-zero positive value to the second weighting factor.

* * * * *